(12) United States Patent
Morita et al.

(10) Patent No.: US 10,898,145 B2
(45) Date of Patent: Jan. 26, 2021

(54) IMAGE DISPLAY DEVICE, IMAGE DISPLAY METHOD, AND IMAGE DISPLAY PROGRAM

(71) Applicant: FUJIFILM CORPORATION, Tokyo (JP)

(72) Inventors: Junya Morita, Kanagawa (JP); Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 6 days.

(21) Appl. No.: 16/435,571

(22) Filed: Jun. 10, 2019

(65) Prior Publication Data

US 2020/0008759 A1 Jan. 9, 2020

(30) Foreign Application Priority Data

Jul. 3, 2018 (JP) .................................. 2018-126969

(51) Int. Cl.
*G06K 9/00* (2006.01)
*A61B 6/03* (2006.01)
*A61B 6/02* (2006.01)
*A61B 6/00* (2006.01)

(52) U.S. Cl.
CPC .............. *A61B 6/032* (2013.01); *A61B 6/025* (2013.01); *A61B 6/5205* (2013.01); *A61B 6/5264* (2013.01)

(58) Field of Classification Search
CPC ....... A61B 6/025; A61B 6/032; A61B 6/5205; A61B 6/5264; A61B 6/463; A61B 6/469; A61B 6/502; G06F 12/0868; G06F 12/0886; G06F 12/0895; G06F 12/123; G06F 12/127; G06T 11/008; G06T 2211/412
See application file for complete search history.

(56) References Cited

U.S. PATENT DOCUMENTS

| 2008/0186311 | A1 | 8/2008 | Claus |
| 2016/0183887 | A1* | 6/2016 | Toba ........................ A61B 6/12 600/424 |
| 2016/0302746 | A1* | 10/2016 | Erhard ................... A61B 6/466 |
| 2017/0071554 | A1* | 3/2017 | Fukuda ................. G06T 11/006 |

FOREIGN PATENT DOCUMENTS

| JP | 2010-194297 A | 9/2010 |
| JP | 2012-70840 A | 4/2012 |
| WO | 2015146166 A1 | 10/2015 |

OTHER PUBLICATIONS

Extended European Search Report dated Nov. 21, 2019, issued in corresponding EP Patent Application No. 19182432.5.

* cited by examiner

*Primary Examiner* — Tom Y Lu
(74) *Attorney, Agent, or Firm* — Solaris Intellectual Property Group, PLLC

(57) ABSTRACT

An image acquisition unit acquires a plurality of projection images corresponding to a plurality of radiation source positions at the time of tomosynthesis imaging, the plurality of projection images being generated by causing an imaging apparatus to perform tomosynthesis imaging in which radiation is emitted to a subject. A structure position specifying unit specifies one structure position in the subject. A display controller specifies projection positions of the structure position in the plurality of projection images, and performs switching display of the plurality of projection images on a display unit so that the projection positions match a predetermined position on the display unit.

21 Claims, 15 Drawing Sheets

IMAGE DISPLAY DEVICE, IMAGE DISPLAY METHOD, AND IMAGE DISPLAY PROGRAM

CROSS REFERENCE TO RELATED APPLICATIONS

The present application claims priority under 35 U.S.C. § 119 to Japanese Patent Application No. 2018-126969 filed on Jul. 3, 2018. The above application is hereby expressly incorporated by reference, in its entirety, into the present application.

BACKGROUND

Technical Field

The present disclosure relates to an image display device, an image display method, and an image display program for displaying a projection image in the case of acquiring a plurality of projection images by imaging a subject at each of a plurality of radiation source positions and generating tomographic images from the plurality of projection images.

Related Art

In recent years, in radiation image capturing apparatuses using radiation such as X-rays and gamma rays, in order to observe an affected part in more detail, tomosynthesis imaging has been proposed in which a radiation source is moved to emit radiation to a subject from a plurality of radiation source positions to perform imaging and a tomographic image is generated by emphasizing a desired tomographic plane from a plurality of projection images acquired by the imaging. In tomosynthesis imaging, a plurality of projection images are acquired by imaging the subject at a plurality of radiation source positions by moving the radiation source in parallel with a radiation detector or so as to draw a circular or elliptical arc according to the characteristics of the imaging apparatus or required tomographic images and the projection images are reconstructed using a reconstruction method, such as a shift addition method, a simple back projection method, or a filtered back projection method (FBP method), to generate a tomographic image. By generating such a tomographic image on a plurality of tomographic planes of the subject, it is possible to separate structures overlapping each other in a depth direction in which the tomographic planes are aligned. Therefore, it is possible to find a lesion that has been difficult to detect in a two-dimensional image acquired by simple imaging in the related art.

On the other hand, the tomosynthesis imaging has a problem that a reconstructed tomographic image is blurred due to the mechanical error of the imaging apparatus and the influence of body movement of the subject due to the time difference of imaging at each of a plurality of radiation source positions. In a case where the tomographic image is blurred as described above, it is difficult to find a lesion such as minute calcification, which is useful for early detection of breast cancer, particularly in a case where the breast is a subject.

For this reason, a method of causing an operator to recognize the body movement of a subject by sequentially displaying a plurality of projection images acquired by tomosynthesis imaging has been proposed (refer to JP2010-194297A).

However, since the tomosynthesis imaging is performed by moving an X-ray source so that X-rays are emitted to the subject from different angles, the position of an X-ray irradiation region in the X-ray detector differs according to the position of the X-ray source. For example, in a case where the X-ray source is located at a position (that is, center position of the movement range) crossing the perpendicular passing through the center of gravity of the detector in the movement path of the X-ray source, the X-ray irradiation region is located at the center of the detector. However, as the X-ray source moves away from the center position, the irradiation range of X-rays moves. Specifically, as viewed from a direction perpendicular to the movement path of the X-ray source, the X-ray irradiation position moves to the right of the detector in a case where the X-ray source is located on the left of the center position, and the X-ray irradiation position moves to the left of the detector in a case where the X-ray source is located on the right of the center position.

For this reason, a method of adjusting the display position of a projection image so that a reference point in a subject region included in the projection image, specifically, the projection position of the center point of the reconstruction range of a tomographic image matches a predetermined position on the display screen of a monitor has been proposed (refer to JP2012-70840A). According to the method disclosed in JP2012-70840A, in a case where a plurality of projection images are sequentially displayed, the subject region does not move on the display screen. Therefore, it is possible to easily observe the body movement of the subject during imaging.

However, in the method disclosed in JP2012-70840A, relatively large body movement, such as the movement of several centimeters of the entire subject, can be observed, but it is difficult to observe relatively small body movement, such as the movement of several millimeters of a structure inside the subject. For example, in a case where a structure with a relatively high contrast is present at a location different from the reference point in a projection image, in the case of sequentially displaying projection images, a structure 100 appears to move even though a reference point 101 does not move, as shown in FIG. 26. For this reason, in the method disclosed in JP2012-70840A, even in a case where body movement occurs, it is difficult to correctly determine whether or not the body movement has actually occurred.

SUMMARY OF THE INVENTION

The present disclosure has been made in view of the above-described circumstances, and the object of the present disclosure is to make it possible to correctly determine whether or not body movement has occurred.

An image display device according to the present disclosure comprises: an image acquisition unit that acquires a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source; a structure position specifying unit that specifies one structure position in the subject; and a display controller that specifies projection positions of the structure position in the plurality of projection images and performs switching display of the plurality of projection images on a display unit such that the projection positions match a predetermined position on the display unit.

"Move the radiation source relative to the detection unit" includes a case of moving only the radiation source, a case of moving only the detection unit, and a case of moving both the radiation source and the detection unit.

"Tomosynthesis imaging" is an imaging method for acquiring a plurality of images corresponding to a plurality of radiation source positions by moving the radiation source relative to the detection unit such that radiation is emitted to the subject at the plurality of radiation source positions according to the movement of the radiation source.

The image display device according to the present disclosure may further comprise a reconstruction unit that generates a tomographic image in at least one tomographic plane of the subject by reconstructing the plurality of projection images. The structure position specifying unit may specify feature points included in the tomographic image, calculate a distribution of signal values of the feature points in a direction in which the tomographic planes are aligned, and specify, as the structure position, a position having a highest signal value or a position having a lowest signal value in the distribution.

In the image display device according to the present disclosure, the structure position specifying unit may calculate the signal value distribution based on other tomographic images having a distance between tomographic planes smaller than that in a case of the tomographic image.

In the image display device according to the present disclosure, the structure position specifying unit may detect a plurality of structure position candidates in the subject and specify the one structure position from the plurality of structure position candidates.

The image display device according to the present disclosure may further comprise a reconstruction unit that generates a tomographic image in at least one tomographic plane of the subject by reconstructing the plurality of projection images. The structure position specifying unit may specify a plurality of feature points included in the tomographic image, calculate a distribution of signal values in a direction in which the tomographic plane is aligned for each of the plurality of feature points, specify a position having a highest signal value or a position having a lowest signal value in the distribution as the structure position candidate for each of the plurality of feature points, and specify a structure position candidate having a highest signal value or a structure position candidate having a lowest signal value, among the plurality of structure position candidates, as the structure position.

In this case, the structure position specifying unit may calculate the signal value distribution based on other tomographic images having a distance between tomographic planes smaller than that in a case of the tomographic image.

In the image display device according to the present disclosure, the structure position specifying unit may specify corresponding points indicating the same structure among the plurality of projection images, reconstruct corresponding points among the plurality of projection images, and specify a position including the corresponding points in the subject as the structure position.

In the image display device according to the present disclosure, the structure position specifying unit may specify a plurality of corresponding points indicating the same structure among the plurality of projection images, reconstruct each of the plurality of corresponding points among the plurality of projection images, specify positions including the plurality of corresponding points in the subject as the plurality of structure position candidates, and specify a structure position candidate having a highest signal value or a structure position candidate having a lowest signal value, among the plurality of structure position candidates, as the structure position.

In the image display device according to the present disclosure, the structure position specifying unit may specify at least one corresponding point indicating the same structure among the plurality of projection images, set a plurality of straight lines connecting corresponding points in the plurality of projection images and a radiation source position at the time of acquiring each of the plurality of projection images, calculates a plurality of first intersections of the plurality of straight lines as viewed from a direction perpendicular to a movement direction of the radiation source, set a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, and specify the structure position based on the reference point and the second intersections.

In the image display device according to the present disclosure, the structure position specifying unit may specify a plurality of corresponding points indicating the same structure among the plurality of projection images, set a plurality of straight lines connecting the plurality of corresponding points in the plurality of projection images and a radiation source position at the time of acquiring each of the plurality of projection images, calculate a plurality of first intersections of the plurality of straight lines as viewed from a direction perpendicular to a movement direction of the radiation source, set a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, specify the plurality of structure position candidates based on the reference point and the second intersections, and specify the structure position from the plurality of structure position candidates based on variations of the plurality of first intersections and the plurality of second intersections for each of the plurality of structure position candidates.

The image display device according to the present disclosure may further comprise a reconstruction unit that generates a tomographic image in at least one tomographic plane of the subject by reconstructing the plurality of projection images. The structure position specifying unit may specify feature points included in the tomographic image, project the feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, reconstruct corresponding points among the plurality of projection images, and specify a position including the corresponding points in the subject as the structure position.

The image display device according to the present disclosure may further comprise a reconstruction unit that generates a tomographic image in at least one tomographic plane of the subject by reconstructing the plurality of projection images. The structure position specifying unit may specify a plurality of feature points included in the tomographic image, project the plurality of feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, reconstruct corresponding points among the plurality of projection images, specify positions including the corresponding points in the subject as the plurality of structure position candidates, and specify a structure position candidate having a highest signal value or a structure position candidate having a lowest signal value, among the plurality of structure position candidates, as the structure position.

The image display device according to the present disclosure may further comprise a reconstruction unit that generates a tomographic image in at least one tomographic plane of the subject by reconstructing the plurality of projection images. The structure position specifying unit may specify a plurality of feature points included in the tomographic image, project the plurality of feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, set a plurality of straight lines connecting the plurality of corresponding points in the plurality of projection images and a radiation source position at the time of acquiring each of the plurality of projection images, calculate a plurality of first intersections of the plurality of straight lines as viewed from a direction perpendicular to a movement direction of the radiation source, set a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, specify the plurality of structure position candidates based on the reference point and the second intersections, and specify the structure position from the plurality of structure position candidates based on variations of the plurality of first intersections and the plurality of second intersections for each of the plurality of structure position candidates.

In the image display device according to the present disclosure, the display controller may perform switching display of only a region with a specific size including the projection positions in the plurality of projection images on the display unit.

In the image display device according to the present disclosure, the display controller may further display a tomographic image of a tomographic plane including the structure position on the display unit.

In the image display device according to the present disclosure, the display controller may display the structure position in the projection image on the display unit such that the structure position in the projection image is emphasized.

In the image display device according to the present disclosure, the subject may be a breast. The image display device according to the present disclosure may further comprise a body movement detection unit that detects body movement of the subject. The structure position specifying unit may specify the structure position in a case where the body movement is detected, and the display controller may perform switching display of the plurality of projection images on the display unit in a case where the body movement is detected. The image display device according to the present disclosure may further comprise: a body movement detection unit that detects body movement of the subject; and a body movement correction unit that performs body movement correction on the projection image in a case where the body movement is detected. The display controller may specify the projection positions in the plurality of projection images on which body movement correction has been performed and perform switching display of the plurality of projection images, on which body movement correction has been performed, on the display unit such that the projection positions match a predetermined position on the display unit.

An image display method according to the present disclosure comprises: acquiring a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source; specifying one structure position in the subject; and specifying projection positions of the structure position in the plurality of projection images and performing switching display of the plurality of projection images on a display unit such that the projection positions match a predetermined position on the display unit.

In addition, a program causing a computer to execute the image display method according to the present invention may be provided.

Another image display device according to the present disclosure comprises: a memory that stores commands to be executed by a computer; and a processor configured to execute the stored commands. The processor executes: a step of acquiring a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source; a step of specifying one structure position in the subject; and a step of specifying projection positions of the structure position in the plurality of projection images and performing switching display of the plurality of projection images on a display unit such that the projection positions match a predetermined position on the display unit.

According to the present disclosure, a plurality of projection images corresponding to a plurality of radiation source positions, which are generated by causing an imaging apparatus to perform tomosynthesis imaging, are acquired. Then, one structure position in the subject is specified, projection positions of the structure position in the plurality of projection images are specified, and switching display of the plurality of projection images is performed on a display unit so that the projection positions match a predetermined position on the display unit. In the case of performing switching display of the projection images as described above, the manner of movement of a structure present at the structure position in the projection image differs depending on whether or not body movement occurs. That is, in a case where body movement does not occur, the structure present at the structure position is present at the projection position of the structure position in each projection image, or is present on a line that passes through the projection position and matches the movement direction of the radiation source. For this reason, in a case where body movement does not occur, in the projection image to be switching-displayed, the structure present at the structure position does not move or moves in the same direction as the movement direction of the radiation source. On the other hand, in a case where body movement occurs, the structure present at the structure position is not necessarily present at the projection position of the structure position in each projection image. For this reason, in a case where body movement occurs, in the projection image to be switching-displayed, the structure present at the structure position moves irregularly in an irregular direction. Therefore, according to the present disclosure, in the projection image to be switching-displayed, whether or not body movement occurs during tomosynthesis imaging can be easily checked by observing how a structure other the structure present at the structure position included in the projection image moves.

DETAILED DESCRIPTION

Figure 1:
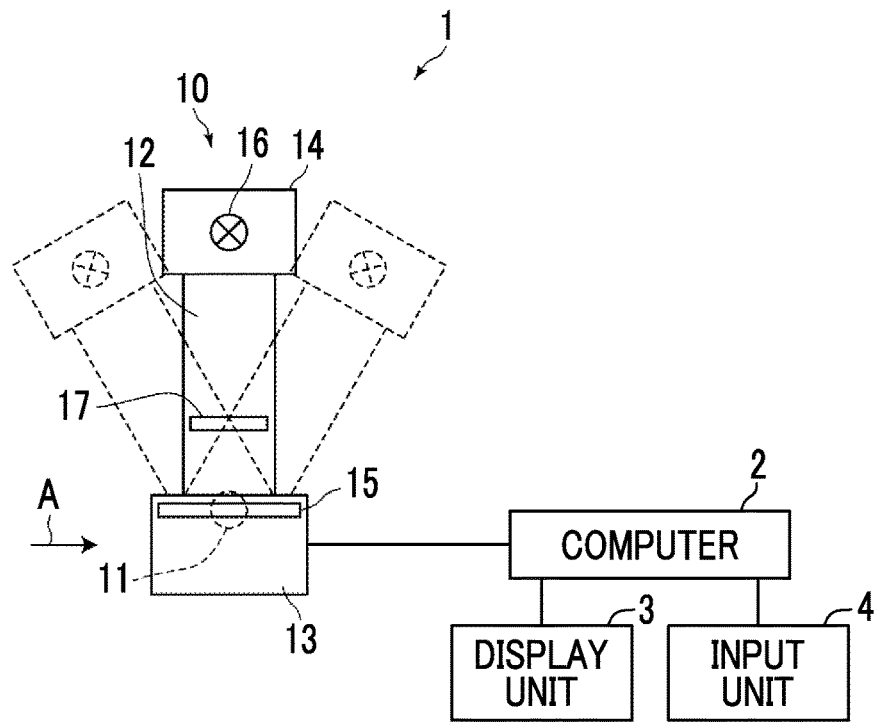
FIG. 1 is a schematic configuration diagram of a radiation image capturing apparatus to which an image display device according to a first embodiment is applied.
Figure 2:
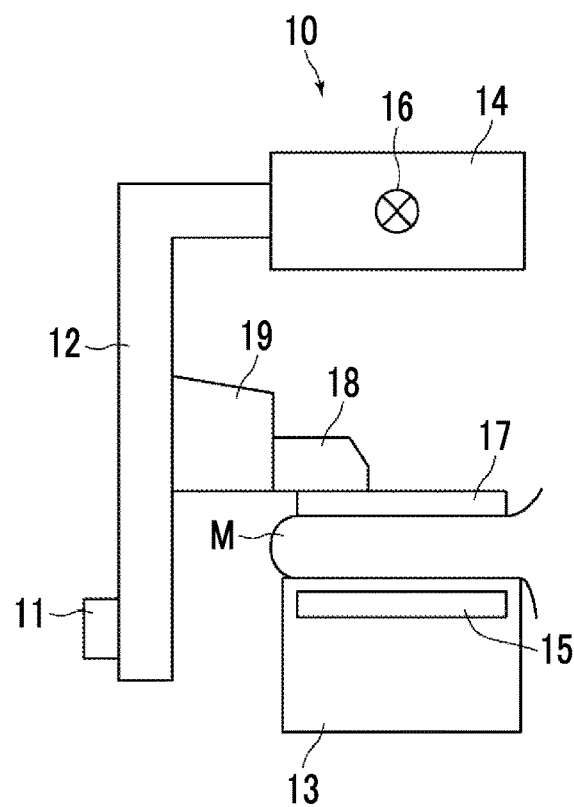
FIG. 2 is a diagram of the radiation image capturing apparatus as viewed from the direction of arrow A in FIG. 1.

Hereinafter, embodiments of the present disclosure will be described with reference to the diagrams. FIG. 1 is a schematic configuration diagram of a radiation image capturing apparatus to which an image display device according to a first embodiment of the present disclosure is applied, and FIG. 2 is a diagram of the radiation image capturing apparatus as viewed from the direction of arrow A in FIG. 1. A radiation image capturing apparatus 1 is a mammography imaging apparatus that acquires a plurality of radiation images, that is, a plurality of projection images, by imaging a breast M, which is a subject, from a plurality of radiation source positions in order to generate a tomographic image by performing tomosynthesis imaging of the breast. As shown in FIG. 1, the radiation image capturing apparatus 1 comprises an imaging unit 10, a computer 2 connected to the imaging unit 10, and a display unit 3 and an input unit 4 connected to the computer 2.

The imaging unit 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the computer 2.

A radiation detector 15, such as a flat panel detector, is comprised inside the imaging table 13. In addition, a circuit board on which a charge amplifier for converting a charge signal read from the radiation detector 15 into a voltage signal, a correlated double sampling circuit for sampling the voltage signal output from the charge amplifier, an AD conversion unit for converting the voltage signal into a digital signal, and the like are provided is provided inside the imaging table 13. The radiation detector 15 corresponds to a detection unit.

The radiation detector 15 can perform recording and reading of a radiation image repeatedly. A so-called direct-type radiation detector that generates an electric charge by directly receiving radiation may be used, or a so-called indirect-type radiation detector that converts radiation into visible light and then converts the visible light into a charge signal may be used. As a method of reading a radiation image signal, it is desirable to use a so-called TFT reading method in which a radiation image signal is read by ON and OFF of a thin film transistor (TFT) switch or a so-called optical reading method in which a radiation image signal is read by emission of reading light. However, other methods may also be used without being limited to the above methods. The radiation detector 15 corresponds to a detection unit.

An X-ray source 16, which is a radiation source, is housed inside the radiation emission unit 14. The timing of emission of X-rays, which are radiations from the X-ray source 16, and X-ray generation conditions in the X-ray source 16, that is, selection of target and filter materials, a tube voltage, an emission time, and the like are controlled by the computer 2.

A compression plate 17 disposed above the imaging table 13 in order to compress the breast M, a support unit 18 for supporting the compression plate 17, and a moving mechanism 19 for moving the support unit 18 in the vertical direction in FIGS. 1 and 2 are provided in the arm unit 12. Information of the distance between the compression plate 17 and the imaging table 13, that is, the compression thickness, is input to the computer 2.

The display unit 3 is a display device, such as a cathode ray tube (CRT) or a liquid crystal monitor, and displays a projection image and a two-dimensional image acquired as will be described later, a generated tomographic image, a message required for the operation, and the like. The display unit 3 may include a speaker for outputting sound.

The input unit 4 is a keyboard, a mouse, or a touch panel type input device, and receives an operation of the radiation image capturing apparatus 1 by the operator. In addition, the input unit 4 receives an input of various kinds of information, such as imaging conditions, and an instruction to modify information, which are required to perform tomosynthesis imaging. In the present embodiment, each unit of the radiation image capturing apparatus 1 operates according to the information input from the input unit 4 by the operator.

An image display program according to the embodiment of the present disclosure is installed in the computer 2. In the present embodiment, the computer may be a workstation or a personal computer that is directly operated by the operator, or may be a server computer connected to these through a network. The image display program is distributed in a state in which the image display program is recorded on a recording medium, such as a digital versatile disc (DVD) or a compact disc read only memory (CD-ROM), and is installed onto the computer from the recording medium. Alternatively, the image display program is stored in a storage device of a server computer connected to the network or in a network storage so as to be accessible from the outside, and is downloaded and installed on the computer as necessary.

Figure 3:
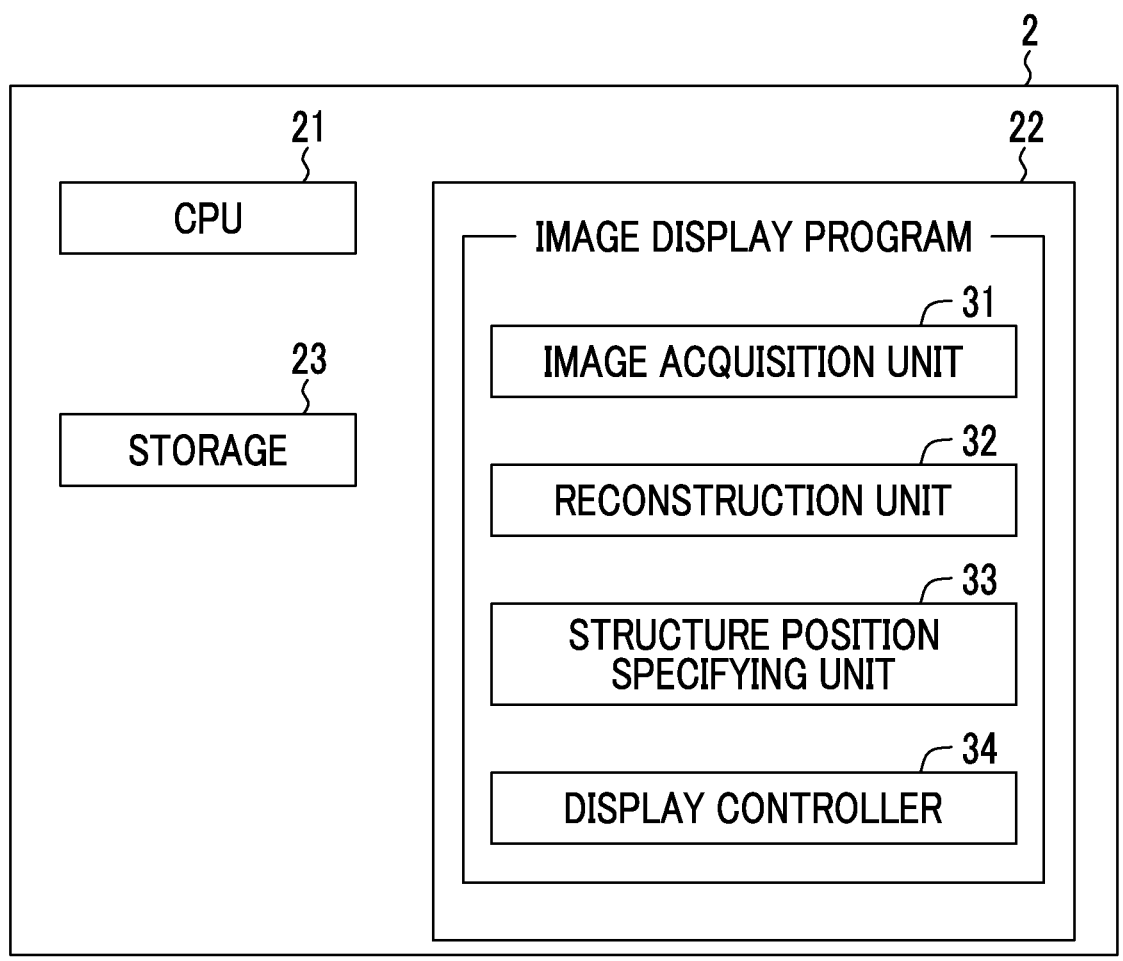
FIG. 3 is a diagram showing the schematic configuration of an image display device realized by installing an image display program on a computer in the first embodiment.

FIG. 3 is a diagram showing the schematic configuration of an image display device realized by installing an image display program on the computer 2. As shown in FIG. 3, the image display device comprises a central processing unit (CPU) 21, a memory 22, and a storage 23 as the configuration of a standard computer.

The storage 23 is a storage device, such as a hard disk or a solid state drive (SSD), and stores various kinds of information including a program for driving each unit of the radiation image capturing apparatus 1 and the image display program. In addition, a projection image acquired by tomosynthesis imaging and a tomographic image generated as will be described later are stored in the storage 23.

The memory 22 temporarily stores programs and the like stored in the storage 23 so that the CPU 21 executes various kinds of processing. As processing to be executed by the CPU 21, the image display program defines: image acquisition processing for acquiring a plurality of projection images of the breast M corresponding to a plurality of radiation source positions by making the radiation image capturing apparatus 1 perform tomosynthesis imaging; reconstruction processing for reconstructing the plurality of projection images to generate a tomographic image in a tomographic plane of the breast M; structure position specifying processing for specifying one structure position in the breast M; and display control processing for specifying projection positions of the structure position in the plurality of projection images and performing switching display of the plurality of projection images on the display unit 3 so that the projection positions match a predetermined position on the display unit 3.

Then, the CPU 21 executes these processes according to the image display program, so that the computer 2 functions as an image acquisition unit 31, a reconstruction unit 32, a structure position specifying unit 33, and a display controller 34. In the present embodiment, the CPU 21 executes the function of each unit according to the image display program. However, as a general-purpose processor that executes software to function as various processing units, a programmable logic device (PLD) that is a processor whose circuit configuration can be changed after manufacturing, such as a field programmable gate array (FPGA), can be used in addition to the CPU 21. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor. As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

Figure 4:
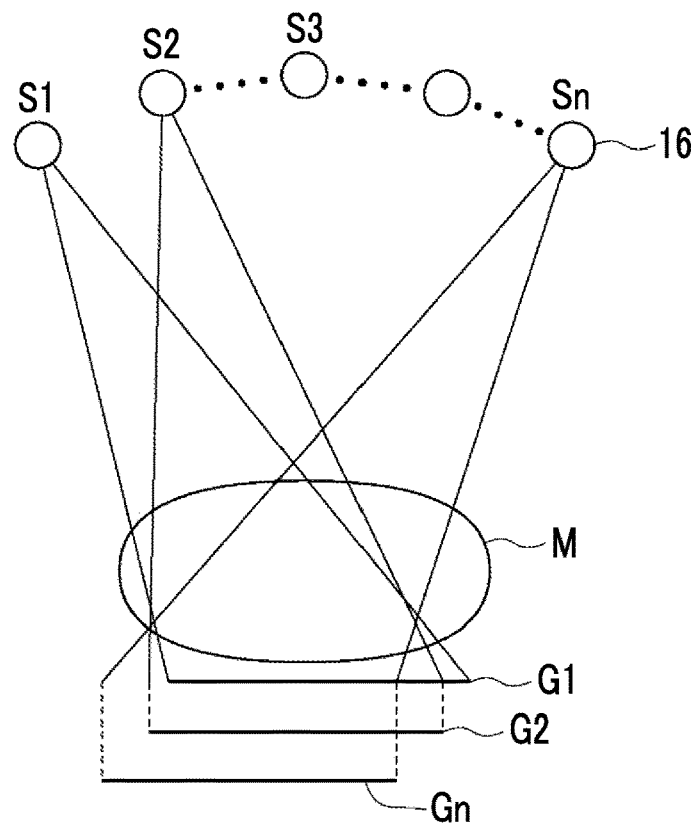
FIG. 4 is a diagram illustrating the acquisition of a projection image.

By rotating the arm unit 12 around the rotary shaft 11 to move the X-ray source 16, X-rays are emitted to the breast M that is a subject at a plurality of radiation source positions according to the movement of the X-ray source 16. Tomosynthesis imaging for detecting the X-rays transmitted through the breast M with the radiation detector 15 is performed by the radiation image capturing apparatus 1. Accordingly, the image acquisition unit 31 acquires a plurality of projection images Gi (i=1 to n, where n is the number of radiation source positions; for example, n=15) at a plurality of radiation source positions. FIG. 4 is a diagram illustrating the acquisition of the projection image Gi. FIG. 4 shows the breast M as viewed from a direction perpendicular to the movement direction of the X-ray source 16. As shown in FIG. 4, the X-ray source 16 is moved to each radiation source position of S1, S2, . . . , Sn, the X-ray source 16 is driven at each radiation source position to irradiate the breast M with X-rays, and the X-rays transmitted through the breast M are detected by the radiation detector 15. As a result, projection images G1, G2, . . . , Gn are acquired corresponding to the radiation source positions S1 to Sn. At each of the radiation source positions S1 to Sn, X-rays of the same dose are emitted to the breast M. The plurality of acquired projection images Gi are stored in the storage 23. The plurality of projection images Gi may be acquired by a program separate from the image display program and stored in the storage 23. In this case, the image acquisition unit 31 reads the plurality of projection images Gi stored in the storage 23 from the storage 23 for reconstruction processing, display, and the like.

The reconstruction unit 32 generates a tomographic image in which a desired tomographic plane of the breast M is emphasized by reconstructing the projection image Gi. Specifically, the reconstruction unit 32 generates a tomographic image Dj (j=1 to m: m is the number of tomographic planes) on each of a plurality of tomographic planes of the breast M by reconstructing the projection image Gi using a known back projection method, such as a shift addition method, a simple back projection method, or a filtered back projection method. The number of tomographic images to be generated may be one.

The structure position specifying unit 33 specifies one structure position in the breast M. In the first embodiment, the structure position specifying unit 33 specifies feature points included in the plurality of tomographic images Dj generated by the reconstruction unit 32, calculates, for the feature points, the distribution of signal values of the feature points in a direction in which the tomographic planes are aligned, and specifies, as a structure position, a position having the highest signal value or a position having the lowest signal value in the calculated distribution. Hereinafter, structure position specifying processing in the first embodiment will be described in detail.

In the first embodiment, first, the structure position specifying unit 33 detects feature point candidates from each of the plurality of tomographic images Dj generated by the reconstruction unit 32. Specifically, edges, intersections of edges, corners of edges, and the like included in the plurality of tomographic images Dj are detected as feature point candidates using an algorithm, such as a Harris's corner detection method, a scale-invariant feature transform (SIFT), a features from accelerated segment test (FAST), or speeded up robust features (SURF). Here, the feature point candidate may be only one pixel. However, a region including a plurality of pixels may be set as the feature point candidate. In a case where the feature point candidate includes a plurality of pixels, the specified structure position also includes a plurality of pixels. In a case where a plurality of feature point candidates are detected in one tomographic image Dj, a feature point candidate having the largest feature amount calculated by the algorithm, among the plurality of feature point candidates, is specified as a feature point candidate of the tomographic image Dj. In addition, the structure position specifying unit 33 determines a feature point candidate having the largest feature amount calculated by the algorithm, among the feature point candidates specified in the plurality of tomographic images Dj, as a feature point to be used in the structure position specifying processing. In addition, in a case where the number of generated tomographic images is one, the structure position specifying unit 33 may detect a feature point from the one tomographic image.

The structure position specifying unit 33 may specify a feature point by displaying the tomographic image Dj on the display unit 3 and receiving the designation of a feature point by the operator using the input unit 4 in the displayed tomographic image Dj. The structure position specifying unit 33 may be made to be able to perform computer-aided diagnosis (CAD) using a discriminator learned by deep learning or the like. Alternatively, the structure position specifying unit 33 may analyze the tomographic image Dj by CAD, detect a region such as a lesion included in the tomographic image Dj, in particular, a region of calcification in the breast M, and specify the position of the detected lesion as a feature point. In addition, a feature point may be specified by generating an MIP image by projecting a plurality of tomographic images Dj using a maximum intensity projection method (MIP method), detecting a feature point from the MW image, and calculating the position of the tomographic plane of the detected feature point. In order to shorten the calculation time of the feature point specifying processing, a feature point included in one tomographic image, among the plurality of tomographic images Dj, may be specified. For example, a feature point may be specified in a tomographic image showing a tomographic plane with the half the compression thickness.

Here, the structure position specifying unit 33 may specify the specified feature point as a structure position, but a feature point specified in a tomographic image of a certain tomographic plane may be a ripple artifact reflecting feature points included in another tomographic plane. Therefore, in the first embodiment, the structure position specifying unit 33 specifies a structure position by searching for specified feature points in a direction in which tomographic planes are aligned (that is, in a depth direction of the breast M viewed from the X-ray source 16).

Figure 5:
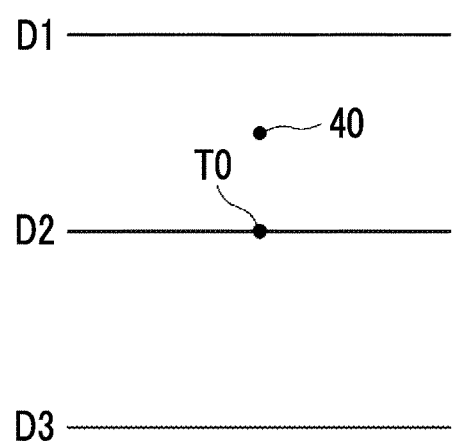
FIG. 5 is a diagram illustrating a search for a feature point.

FIG. 5 is a diagram illustrating a search for feature points. In FIG. 5, in order to simplify the description, it is assumed that only three tomographic images D1 to D3 are shown and a feature point T0 is specified in the tomographic image D2. In addition, it is assumed that the distance between tomographic planes of the tomographic images Dj is 1 mm. In a case where the feature point T0 is specified in the tomographic image D2 as described above, the feature point T0 may be a ripple artifact. For example, as shown in FIG. 5, a ripple artifact of a structure 40 present between a tomographic plane expressed by the tomographic image D1 and a tomographic plane expressed by the tomographic image D2 may be the feature point T0 included in the tomographic image D2.

For this reason, the structure position specifying unit 33 instructs the reconstruction unit 32 to generate tomographic images Dsj having a distance between tomographic planes smaller than that in a case of the tomographic image Dj. The tomographic images Dsj correspond to other tomographic images. In this case, in a case where the tomographic image Dsj is generated by the filtered back projection method, an artifact such as overshoot or undershoot occurs in the tomographic image Dsj due to the influence of the filter. For this reason, the reconstruction unit 32 reconstructs the projection image Gi by using a back projection method (for example, a simple back projection method), in which a filter is not used, to generate the tomographic image Dsj.

Figure 6:
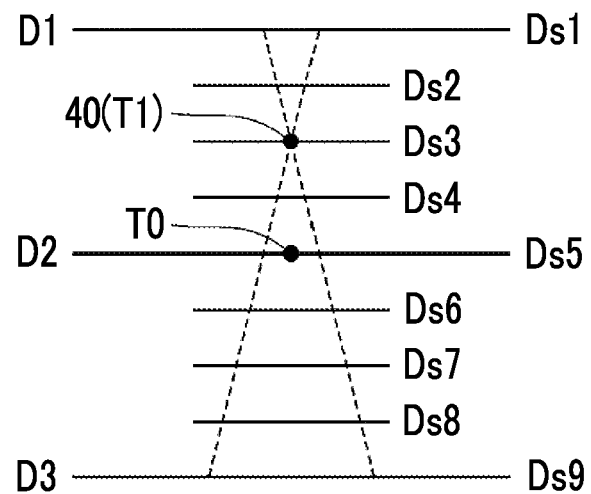
FIG. 6 is a diagram illustrating the generation of tomographic images having a small distance therebetween.

FIG. 6 is a diagram illustrating the generation of tomographic images having a small distance therebetween. In FIG. 6, the distance between tomographic planes of the tomographic images Dsj is 0.25 mm, and the tomographic image Ds1 corresponds to the tomographic image D1, the tomographic image Ds5 corresponds to the tomographic image D2, and the tomographic image Ds9 corresponds to the tomographic image D3. It is assumed that an image of the structure 40 is included in the tomographic image Ds3. It is preferable that the distance between tomographic planes of the tomographic images Dsj is smaller. In order to shorten the calculation time for reconstruction, the tomographic image Dsj may be generated only in a region within a predetermined range including the feature point T0. Needless to say, the tomographic image Dsj may be generated so as to have the same size as the tomographic image Dj.

Here, each tomographic image Dsj includes a ripple artifact of the structure 40. As shown by the broken line in FIG. 6, the ripple artifact expands as a distance from the tomographic image Ds3 including the structure C0 increases. For this reason, the pixel value of the ripple artifact decreases with a distance from the tomographic image Ds3 including the structure C0. Therefore, the structure position specifying unit 33 calculates pixel values at positions corresponding to the feature point T0 included in the tomographic image D2 (tomographic image Ds5) in all the tomographic images Dsj, and generates a profile of pixel values in a direction in which the tomographic planes are aligned (hereinafter, referred to as a depth direction).

Figure 7:
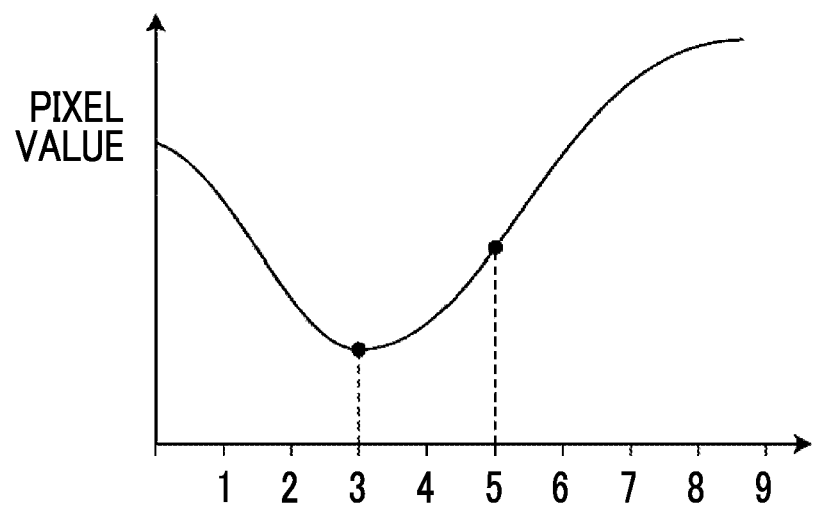
FIG. 7 is a diagram showing a profile of pixel values.

FIG. 7 is a diagram showing a profile of pixel values. In FIG. 7, the horizontal axis indicates the position of the tomographic plane of the tomographic image Dsj, and the vertical axis indicates the pixel value. In FIG. 7, the position of the tomographic plane is indicated by a number given to the tomographic image Dsj. In addition, in FIG. 7, a pixel value at a position between tomographic planes is interpolated by pixel values of adjacent tomographic planes. As shown in FIG. 7, in a case where the structure 40 is present in a tomographic image other than the tomographic image Ds5 (tomographic image D2) among the tomographic images Dsj, the pixel value of a pixel corresponding to the feature point T0 in the tomographic image is smaller than the feature point T0 specified in the tomographic image D2 (tomographic image Dj5). Therefore, the structure position specifying unit 33 specifies, as a structure position T1, a pixel position corresponding to the feature point T0 in the tomographic image Dsj (here, the tomographic image Ds3) that is a minimum value in the profile of pixel values. In addition, although this depends on the type of a structure that is a feature point, a position corresponding to the feature point T0 in a tomographic image in which the profile of pixel values has a maximum value may be specified as the structure position T1.

The display controller 34 specifies projection positions in a plurality of projection images Gi of the structure position T1 specified by the structure position specifying unit 33, and performs switching display of the plurality of projection images Gi on the display unit 3 so that the projection positions match a predetermined position on the display unit 3.

Figure 8:
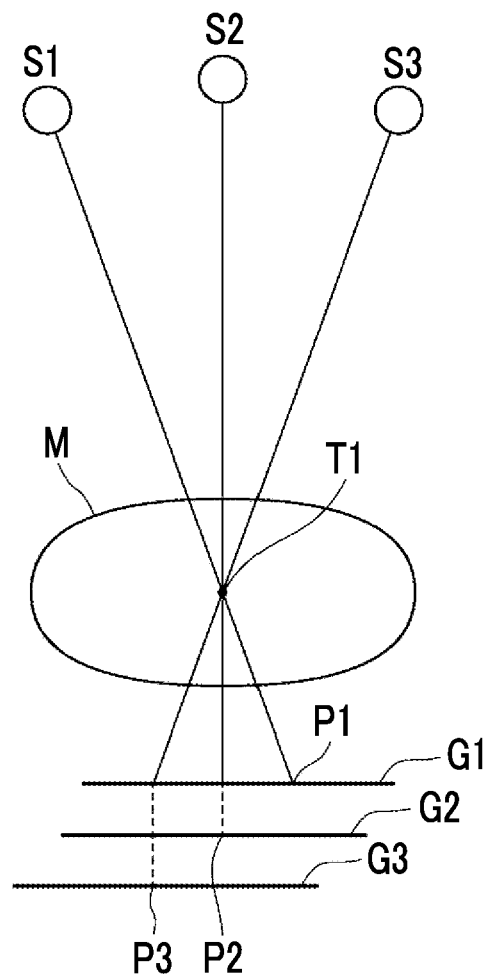
FIG. 8 is a diagram illustrating the specification of a projection position of a structure position in a projection image.

FIG. 8 is a diagram illustrating the specification of a projection position of a structure position in a projection image. In FIG. 8, in order to simplify the description, specification of projection positions in three projection images G1 to G3 corresponding to three radiation source positions S1 to S3 will be described. In FIG. 8, for the sake of description, the projection images G1 to G3 are shown so as to be present on different planes. In practice, however, the projection images G1 to G3 are present on the same plane. As shown in FIG. 8, at the time of imaging, the structure position T1 included in the breast M is projected to positions P1 to P3 in the projection images G1 to G3. Here, the radiation source positions S1 to S3 and the position in the three-dimensional space of the structure position T1 in the breast M are known. In addition, the position of the detection surface of the radiation detector 15 where the projection images G1 to G3 are generated is also known. Therefore, the structure position specifying unit 33 specifies the projection positions P1 to P3 by calculating the projection positions P1 to P3 of the structure position T1 in the projection images G1 to G3 based on the radiation source positions S1 to S3 and the position in the three-dimensional space of the structure position T1 in the breast M and the position of the detection surface of the radiation detector 15 where the projection images G1 to G3 are generated.

Figure 9:
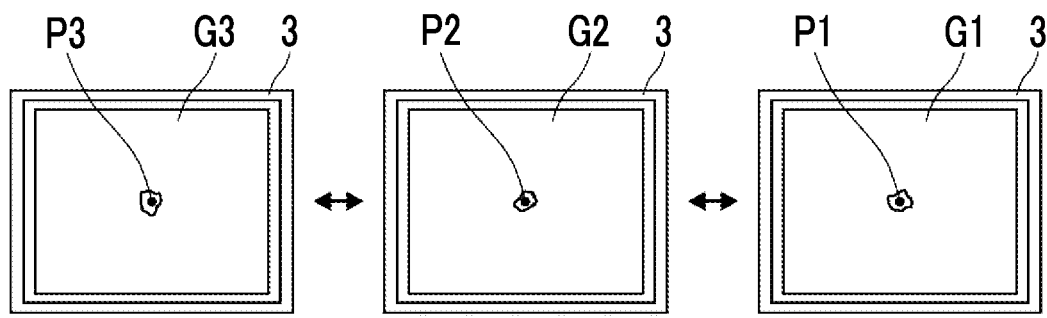
FIG. 9 is a diagram illustrating the switching display of projection images.

Then, the display controller 34 performs switching display of the projection images G1 to G3 on the display unit 3. In this case, the display controller 34 matches the projection positions P1 to P3 of the structure position T1 in the projection images G1 to G3 with predetermined positions on the display unit 3. FIG. 9 is a diagram illustrating the switching display of projection images. FIG. 9 shows a state in which the projection positions P1 to P3 of the structure position T1 in the projection images G1 to G3 are displayed so as to match the center position (that is, the intersection of diagonals of the screen) of the display unit 3. The display controller 34 may perform switching display of the projection images G1 to G3 according to the operator's instruction through the input unit 4, or may perform switching display of the projection images G1 to G3 at predetermined time intervals.

Figure 10:
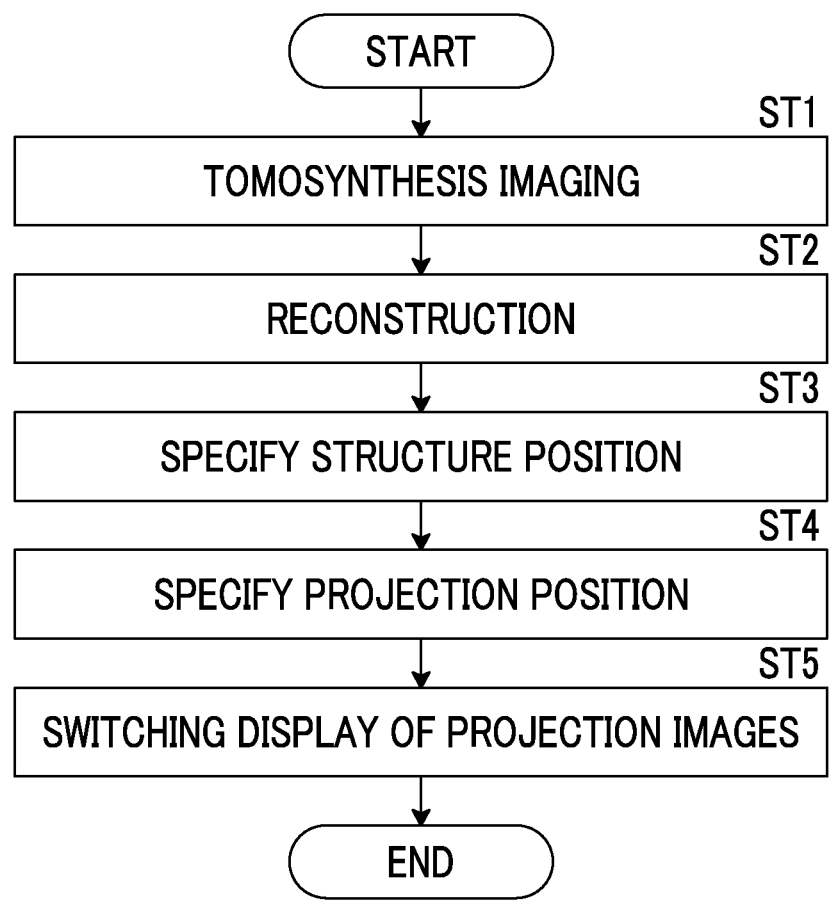
FIG. 10 is a flowchart showing the process performed in the first embodiment.

Next, the process performed in the first embodiment will be described. FIG. 10 is a flowchart showing the process performed in the first embodiment. Since the present disclosure is characterized in that a projection image is displayed, only processing for displaying a projection image will be described herein, and the description of reconstruction processing using a plurality of projection images will be omitted. In a case where the input unit 4 receives an operator's instruction to start the process, tomosynthesis imaging is performed and the image acquisition unit 31 acquires a plurality of projection images Gi (step ST1). Then, the reconstruction unit 32 reconstructs the plurality of projection images Gi to generate the tomographic image Dj in at least one tomographic plane of the breast M (step ST2).

Then, the structure position specifying unit 33 specifies one structure position T1 in the breast M using the tomographic image (step ST3). Then, the display controller 34 specifies projection positions of the structure position T1 in the plurality of projection images Gi (step ST4), performs switching display of the plurality of projection images Gi on the display unit 3 so that the projection positions match a predetermined position on the display unit 3 (step ST5), and the process is ended.

As described above, in the first embodiment, one structure position T1 in the breast M is specified, projection positions of the structure position T1 in a plurality of projection images Gi are specified, and switching display of the plurality of projection images Gi is performed on the display unit 3 so that the projection positions match a predetermined position on the display unit 3.

Figure 11:
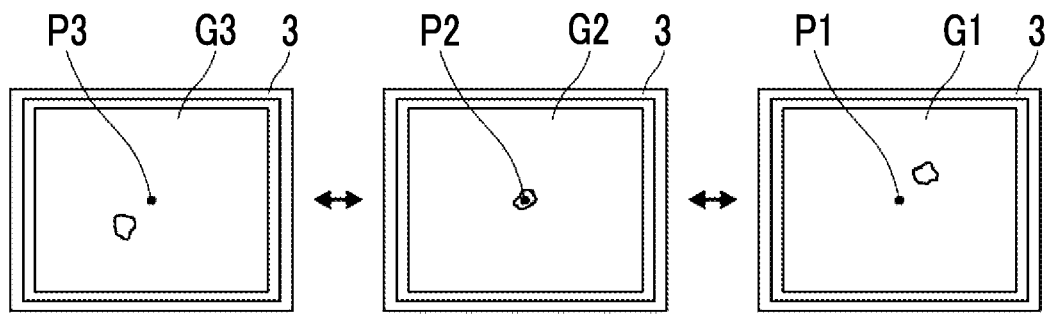
FIG. 11 is a diagram illustrating the switching display of projection images in a case where body movement occurs.

In the case of performing switching display of the projection image Gi as described above, the manner of movement of a structure present at the structure position T1 in the projection image Gi to be switching-displayed differs depending on whether or not body movement occurs. That is, in a case where body movement of the breast M does not occur during tomosynthesis imaging, the structure present at the structure position T1 is present at the projection position of the structure position T1 in each projection image Gi, or is present on a line that passes through the projection position and matches the movement direction of the X-ray source 16. Therefore, in the case of performing switching display of the projection images Gi so that the projection positions match a predetermined position on the display unit 3, the structure present at the projection position of the structure position T1 does not move as shown in FIG. 9, or moves in the movement direction of the X-ray source 16 by an almost fixed movement amount corresponding to the distance between radiation source positions. On the other hand, in a case where body movement occurs, the structure present at the structure position T1 is not necessarily present at the projection position of the structure position T1 in each projection image Gi. For this reason, in a case where body movement occurs, in the projection image Gi switching-displayed so that the projection positions match a predetermined position on the display unit 3, the structure present at the structure position T1 moves in an irregular direction by an irregular movement amount, as shown in FIG. 11.

Therefore, in the projection image Gi to be switching-displayed, whether or not body movement occurs during tomosynthesis imaging can be easily checked by observing how the structure present at the structure position T1 included in the projection image Gi moves.

In the first embodiment described above, the structure position specifying unit 33 specifies the structure position T1 by generating the tomographic image Dsj with a distance between tomographic planes that is smaller than that in the case of reconstructing the tomographic image Dj. However, the present disclosure is not limited thereto. The feature point T0 detected in the tomographic image Dj may be used as the structure position T1.

In the first embodiment described above, the structure position specifying unit 33 may detect a plurality of structure position candidates in the breast M from the tomographic image Dj and specify one structure position from the plurality of structure position candidates. In this case, the structure position specifying unit 33 specifies a plurality of feature points included in the plurality of tomographic images Dj. Then, for each of the plurality of feature points, as shown in FIG. 7, a profile of pixel values in a direction in which tomographic planes are aligned (hereinafter, referred to as a depth direction) is generated. In addition, the structure position specifying unit 33 specifies a position corresponding to the feature point in the tomographic image Dsj, which is a minimum value in the profile of respective feature points, as a structure position candidate. That is, one structure position candidate is specified for each of a plurality of feature points. In addition, the structure position specifying unit 33 determines a structure position candidate having a minimum pixel value, among the plurality of structure position candidates, as a structure position.

Next, a second embodiment of the present disclosure will be described. The configuration of an image display device according to the second embodiment is the same as the configuration of the image display device according to the first embodiment, and only the processing performed by the structure position specifying unit 33 is different. Accordingly, the detailed description of the configuration will be omitted herein. In the first embodiment described above, a structure position is specified using a tomographic image. However, the second embodiment is different from the first embodiment in that a structure position is specified using a projection image.

In the second embodiment, first, the structure position specifying unit 33 specifies corresponding points that are common structures included in a plurality of projection images Gi. Specifically, similarly to the detection of feature points from the tomographic image in the first embodiment described above, at least one corresponding point that is a structure in the projection image Gi, such as an edge, an intersection of edges, and a corner of an edge, included in the projection image Gi is specified using an algorithm, such as the Harris's corner detection method, the SIFT, the FAST, or the SURF. Here, it is assumed that one corresponding point is specified. Here, the corresponding point may be only one pixel. However, a region including a plurality of pixels may be set as the corresponding point. In a case where the corresponding point includes a plurality of pixels, the specified structure position also includes a plurality of pixels.

Similarly to the specification of feature points in the first embodiment, the corresponding point may be specified by analyzing the projection image Gi by CAD. Alternatively, the corresponding point may be specified by displaying the projection image Gi on the display unit 3 and receiving the designation of the corresponding point by the operator.

Figure 12:
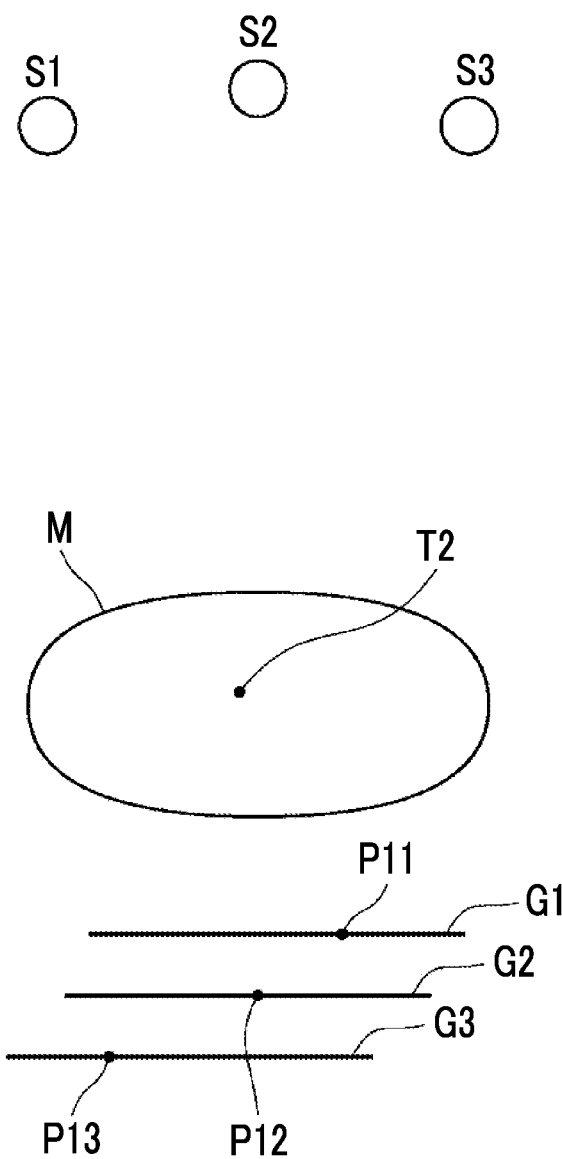
FIG. 12 is a diagram illustrating the specification of a position in the three-dimensional space of a structure, which is expressed by corresponding points in a breast, as a structure position.

Then, by back-projecting the corresponding point detected in the projection image Gi, the structure position specifying unit 33 specifies the position in the three-dimensional space of a structure, which is expressed by the corresponding points in the breast M, as a structure position. In this case, the structure position specifying unit 33 may give an instruction to the reconstruction unit 32 so that the reconstruction unit 32 back-projects the corresponding points. FIG. 12 is a diagram illustrating the specification of a position in the three-dimensional space of a structure, which is expressed by corresponding points in the breast M, as a structure position. In FIG. 12, in order to simplify the description, specification of a structure position using the three projection images G1 to G3 corresponding to the three radiation source positions S1 to S3 will be described. In FIG. 12, for the sake of description, the projection images G1 to G3 are shown so as to be present on different planes. In practice, however, the projection images G1 to G3 are present on the same plane. As shown in FIG. 12, a structure position T2 expressed by corresponding points P11, P12, and P13 in the breast M is specified by back-projecting the corresponding point P11 in the projection image G1, the corresponding point P12 in the projection image G2, and the corresponding point P13 in the projection image G3. By the back projection, it is possible to calculate the tomographic plane where the structure position T2 is present and the two-dimensional position in the tomographic plane. As a result, it is possible to specify the coordinate position of the structure position T2 in the three-dimensional space.

In the second embodiment, the tomographic image Dj is not used in a case where the structure position specifying unit 33 specifies a structure position. Therefore, the processing for specifying the structure position can be performed at high speed.

Figure 13:
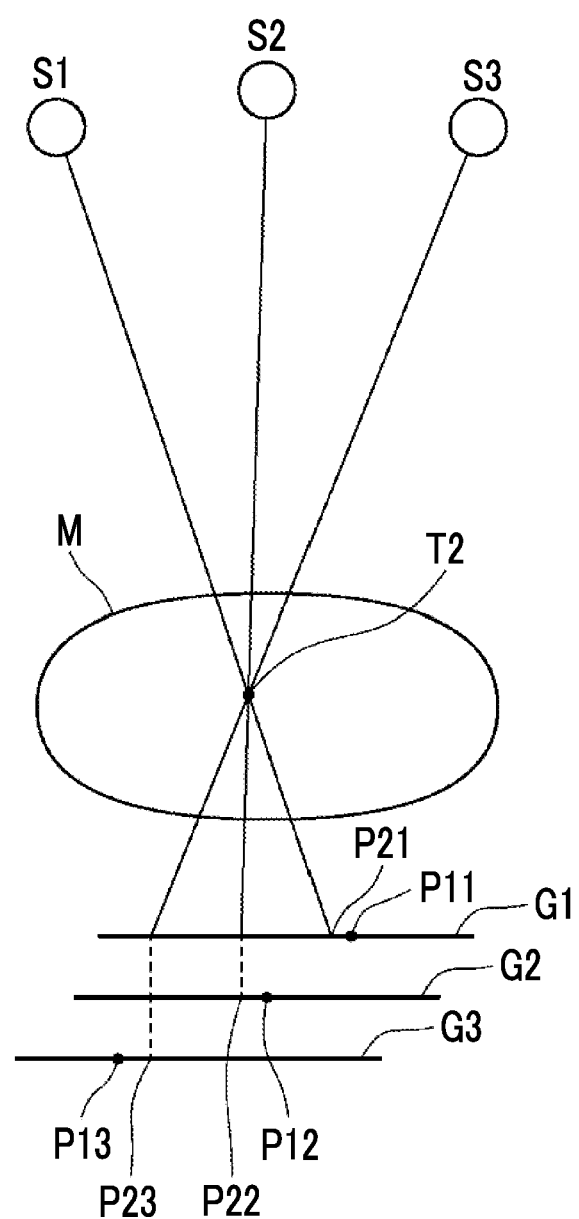
FIG. 13 is a diagram illustrating the specification of a projection position of a structure position.

In the second embodiment, the display controller 34 specifies projection positions P21, P22, and P23 on the projection images G1 to G3 of the structure position T2 specified by the structure position specifying unit 33. FIG. 13 is a diagram illustrating the specification of a projection position of the structure position T2. In FIG. 13, in order to simplify the description, specification of projection positions of the structure position T2 in the three projection images G1 to G3 corresponding to the three radiation source positions S1 to S3 will be described. In FIG. 13, for the sake of description, the projection images G1 to G3 are shown so as to be present on different planes. In practice, however, the projection images G1 to G3 are present on the same plane. As shown in FIG. 13, the structure position T2 is projected to positions P21 to P23 in the projection images G1 to G3. The radiation source positions S1 to S3 and the position of the structure position T2 in the three-dimensional space are known. In addition, the position of the detection surface of the radiation detector 15 where the projection images G1 to G3 are generated is also known. Therefore, the display controller 34 specifies the projection positions P21 to P23 by calculating the projection positions P21 to P23 of the structure position T2 in the projection images G1 to G3 based on the radiation source positions S1 to S3 and the position of the structure position T2 in the three-dimensional space and the position of the detection surface of the radiation detector 15 where the projection images G1 to G3 are generated.

In the second embodiment, at the time of switching display of the projection image Gi, the display controller 34 displays the projection positions P21 to P23 of the structure position T2 in the projection images G1 to G3 so as to match the center position (that is, the intersection of diagonals of the screen) of the display unit 3.

Figure 14:
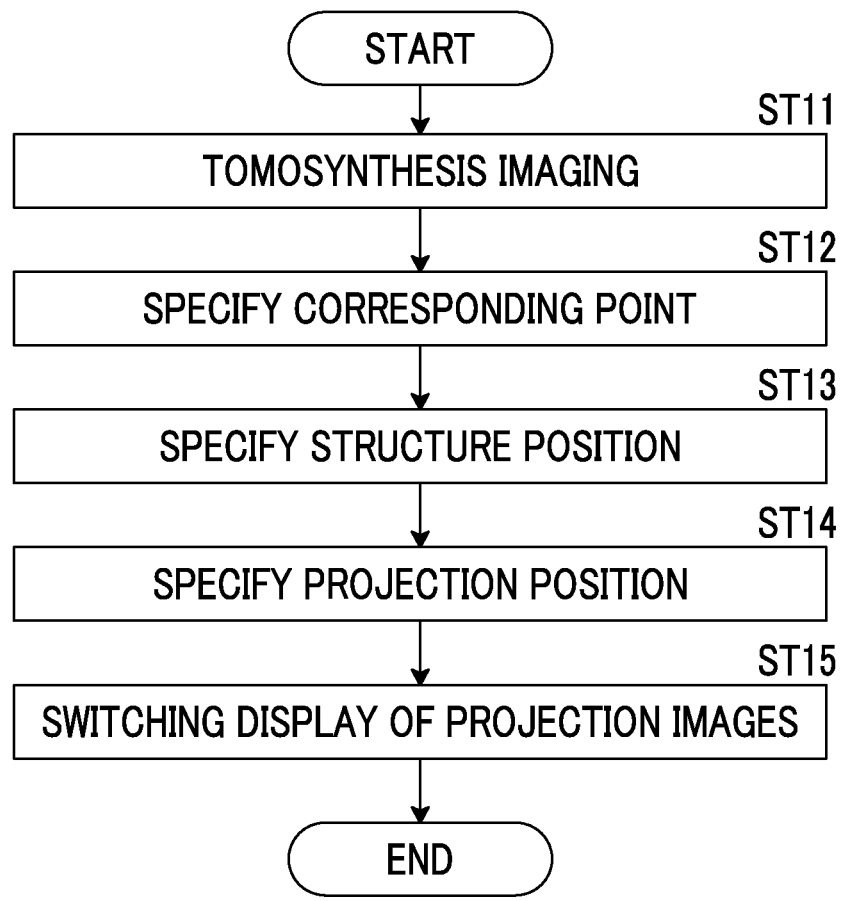
FIG. 14 is a flowchart showing the process performed in a second embodiment.

Next, the process performed in the second embodiment will be described. FIG. 14 is a flowchart showing the process performed in the second embodiment. Since the present disclosure is characterized in that a projection image is displayed, only processing for displaying a projection image will be described herein, and the description of reconstruction processing using a plurality of projection images will be omitted. In a case where the input unit 4 receives an operator's instruction to start the process, tomosynthesis imaging is performed and the image acquisition unit 31 acquires a plurality of projection images Gi (step ST11).

Then, the structure position specifying unit 33 specifies corresponding points in the projection image Gi (step ST12), and specifies one structure position T2 in the breast M by back-projecting the corresponding points (step ST13). Then, the display controller 34 specifies projection positions of the structure position T2 in a plurality of projection images Gi (step ST14), performs switching display of the plurality of projection images Gi on the display unit 3 so that the projection positions match a predetermined position on the display unit 3 (step ST15), and the process is ended.

In the second embodiment described above, a plurality of structure position candidates in the breast M may be detected, and one structure position may be specified from the plurality of structure position candidates. In this case, the structure position specifying unit 33 specifies a plurality of corresponding points indicating the same structure among a plurality of projection images Gi, reconstructs each of the plurality of corresponding points among the plurality of projection images Gi, and specifies positions including the plurality of corresponding points in the breast M as a plurality of structure position candidates. Then, the structure position specifying unit 33 specifies a structure position candidate having the highest signal value or a structure position candidate having the lowest signal value, among the plurality of structure position candidates, as a structure position.

Next, a third embodiment of the present disclosure will be described. The configuration of an image display device according to the third embodiment is the same as the configuration of the image display device according to the first embodiment, and only the processing performed by the structure position specifying unit 33 is different. Accordingly, the detailed description of the configuration will be omitted herein. In the first embodiment described above, a structure position is specified using a tomographic image. However, the third embodiment is different from the first embodiment in that a structure position specified in a tomographic image is projected onto a projection image, corresponding points are specified in a region including the projection position of the structure position, and a structure position is further specified in the tomographic image using the corresponding points.

Figure 15:
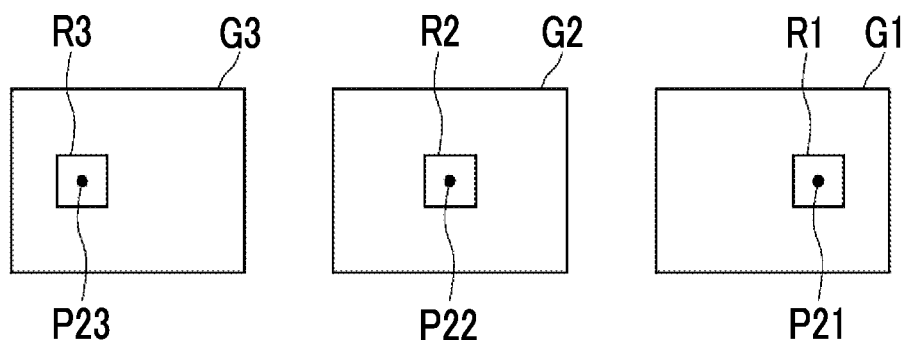
FIG. 15 is a diagram illustrating the setting of a region including a feature projection position.

In the third embodiment, first, the structure position specifying unit 33 specifies the structure position T1 from the tomographic image Dj as in the first embodiment. In the third embodiment, since the structure position T1 is not a final structure position, the structure position T1 is referred to as a feature point T11. Then, the structure position specifying unit 33 projects the feature point T11 onto the projection image Gi, as in the display controller 34 in the first embodiment. In the third embodiment, the structure position specifying unit 33 sets a region, which includes the projection position (hereinafter, referred to as a feature projection position) of the feature point T11 projected onto the projection image Gi, in the projection image Gi. FIG. 15 is a diagram illustrating the setting of a region including a feature projection position. In FIG. 15, setting of regions in the three projection images G1 to G3 will be described for the sake of explanation. As shown in FIG. 15, the structure position specifying unit 33 sets regions R1 to R3 having predetermined sizes centered on the feature projection positions P21 to P23 in the projection images G1 to G3.

Then, the structure position specifying unit 33 specifies a corresponding point that is a common structure included in a region Ri set in each of the plurality of projection images Gi. Specifically, similarly to the detection of corresponding points in the second embodiment described above, at least one corresponding point that is a structure in the region Ri, such as an edge, an intersection of edges, and a corner of an edge, included in the region Ri in each projection image Gi is specified using an algorithm, such as the Harris's corner detection method, the SIFT, the FAST, or the SURF. Similarly to the specification of feature points in the first embodiment, the corresponding point may be specified by analyzing the projection image Gi by CAD. Alternatively, the corresponding point may be specified by displaying the projection image Gi on the display unit 3 and receiving the designation of the corresponding point by the operator.

Here, the corresponding point may be only one pixel. However, a region including a plurality of pixels may be set as the corresponding point. In a case where the corresponding point includes a plurality of pixels, the specified structure position also includes a plurality of pixels. As described above, by specifying the corresponding point in the region Ri set in each of the plurality of projection images Gi, it is possible to reduce the amount of calculation compared with that in a case where the corresponding point is specified in the entire projection image Gi. As a result, the processing for specifying the corresponding point can be performed at high speed.

Then, by back-projecting the corresponding point detected in the region Ri, the structure position specifying unit 33 specifies the position in the three-dimensional space of a structure, which is expressed by the corresponding points in the breast M, as a structure position. The display controller 34 specifies a projection position on the projection image of the structure position specified by the structure position specifying unit 33. Since the specification of the structure position and the specification of the projection position in the third embodiment are the same as those in the second embodiment except that the corresponding points in the region Ri are used, the detailed description thereof will be omitted herein.

Figure 16:
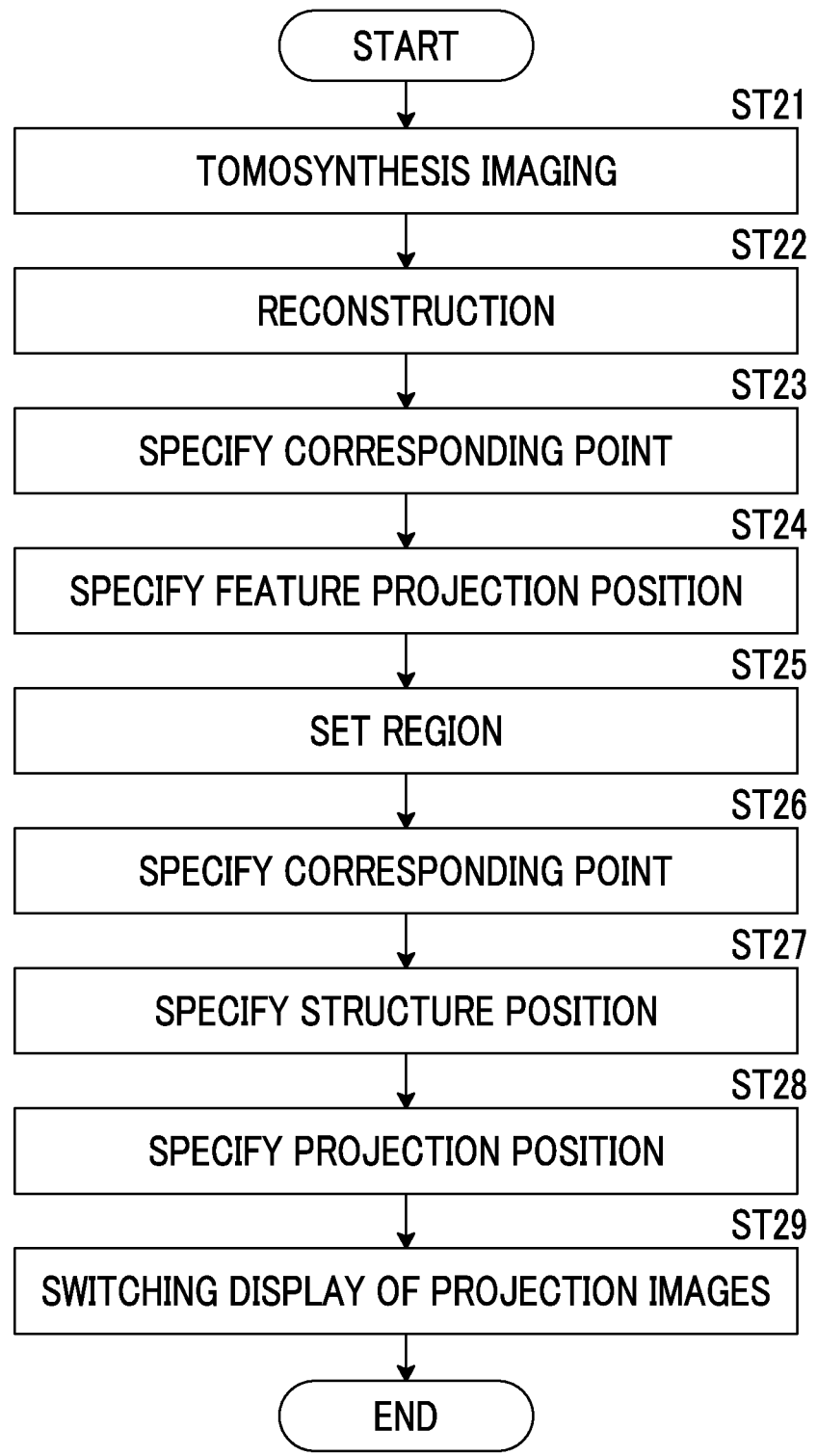
FIG. 16 is a flowchart showing the process performed in a third embodiment.

Next, the process performed in the third embodiment will be described. FIG. 16 is a flowchart showing the process performed in the third embodiment. Since the present disclosure is characterized in that a projection image is displayed, only processing for displaying a projection image will be described herein, and the description of reconstruction processing using a plurality of projection images will be omitted. In a case where the input unit 4 receives an operator's instruction to start the process, tomosynthesis imaging is performed and the image acquisition unit 31 acquires a plurality of projection images Gi (step ST21). Then, the reconstruction unit 32 reconstructs the plurality of projection images Gi to generate a tomographic image in at least one tomographic plane of the breast M (step ST22).

Then, the structure position specifying unit 33 specifies one feature point T11 in the breast M using the tomographic image (step ST23), and specifies feature projection positions that are projection positions of the feature point T11 in the plurality of projection images Gi (step ST24). Then, the structure position specifying unit 33 sets the regions Ri including the feature projection positions in the projection images Gi (step ST25), and specifies corresponding points between the regions Ri (step ST26).

Then, the structure position specifying unit 33 specifies one structure position in the breast M by back-projecting the corresponding points (step ST27). Then, the display controller 34 specifies projection positions of the structure position in the plurality of projection images Gi (step ST28), performs switching display of the plurality of projection images Gi on the display unit 3 so that the projection positions match a predetermined position on the display unit 3 (step ST29), and the process is ended.

In the third embodiment described above, the structure position specifying unit 33 may detect a plurality of structure position candidates in the breast M from the tomographic image Dj and specify one structure position from the plurality of structure position candidates. Hereinafter, the specification of one structure position from a plurality of structure position candidates in the third embodiment will be described.

First, the structure position specifying unit 33 specifies a plurality of feature points included in the plurality of tomographic images Dj. Then, each of the plurality of feature points is projected onto the projection image Gi. Then, the structure position specifying unit 33 sets a region including feature projection positions, which are projection positions of a plurality of feature points projected onto the projection image Gi, in the projection image Gi. Then, the structure position specifying unit 33 specifies corresponding points that are common structures included in a plurality of regions set in the plurality of projection images Gi. Then, by back-projecting the corresponding points detected in the plurality of regions, the structure position specifying unit 33 calculates the position in the three-dimensional space of a structure, which is expressed by the corresponding points in the breast M, as a structure position candidate. Then, the structure position specifying unit 33 specifies a structure position candidate having the highest signal value or a structure position candidate having the lowest signal value, among the plurality of structure position candidates, as a structure position.

Next, a fourth embodiment of the present disclosure will be described. In the second embodiment described above, in the case of detecting a plurality of structure position candidates and specifying one structure position from the plurality of structure position candidates, a plurality of corresponding points among the plurality of projection images Gi are reconstructed, and a position including the plurality of corresponding points in the breast M is specified as a structure position candidate. In the fourth embodiment, a plurality of straight lines connecting corresponding points in a plurality of projection images and radiation source positions at the time of acquiring the plurality of projection images are set, and a structure position is specified based on the intersection of the plurality of straight lines.

Figure 17:
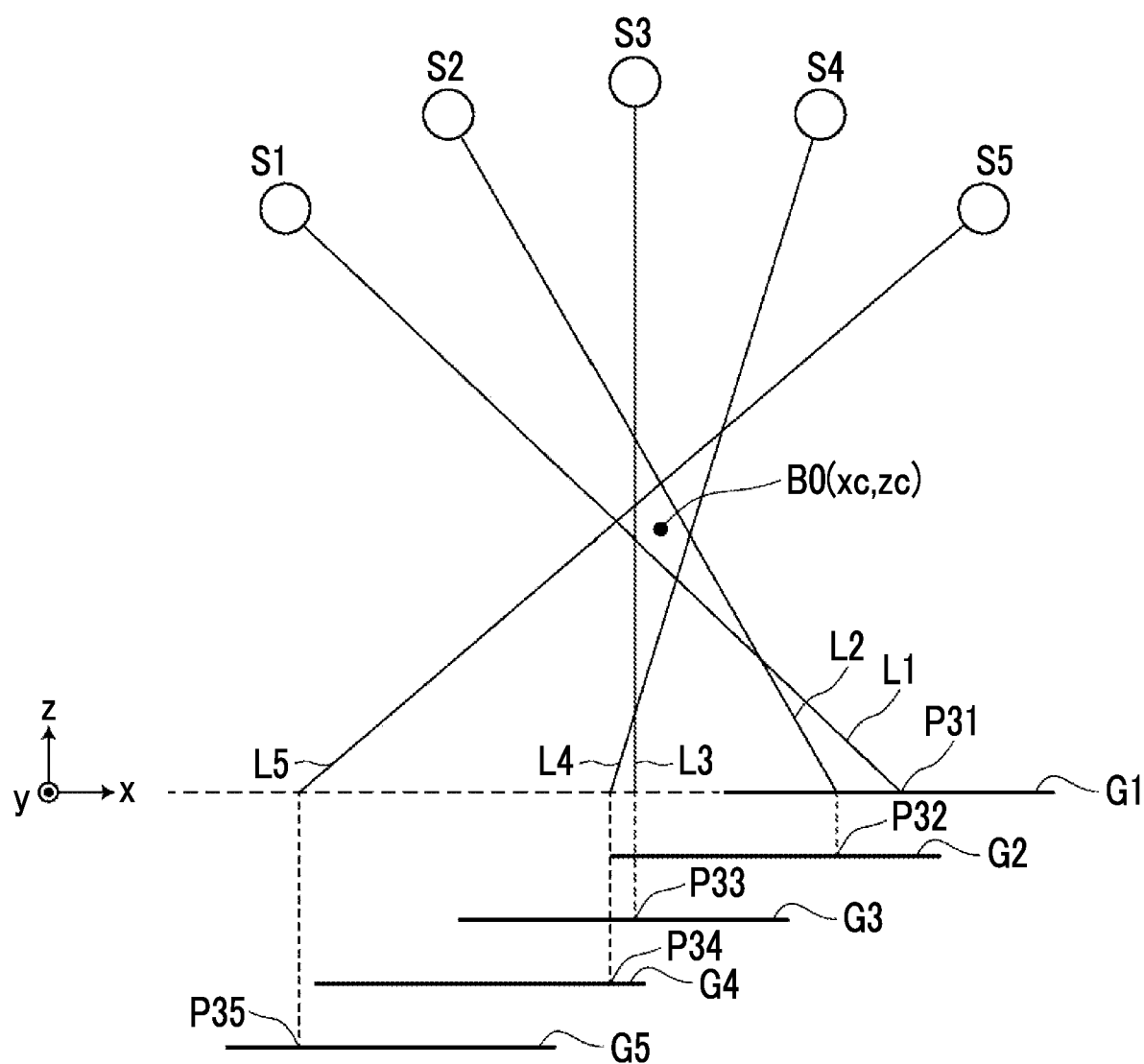
FIG. 17 is a diagram illustrating the specification of a structure position in a fourth embodiment.

FIG. 17 is a diagram illustrating the specification of a structure position in the fourth embodiment. In FIG. 17, a coordinate system is set in which a horizontal direction is an x direction, a vertical direction is a z direction, and a direction perpendicular to the paper is a y direction. In FIG. 17, in order to simplify the description, detection of projection positions from five projection images G1 to G5 corresponding to five radiation source positions S1 to S5 will be described. In FIG. 17, for the sake of description, the projection images G1 to G5 are shown so as to be present on different planes. In practice, however, the projection images G1 to G5 are present on the same plane. In FIG. 17, it is assumed that corresponding points P31 to P35 are specified in the projection images G1 to G5.

In the fourth embodiment, the structure position specifying unit 33 sets a straight line L1 connecting the corresponding point P31 of the projection image G1 and the radiation source position S1 to each other, a straight line L2 connecting the corresponding point P32 of the projection image G2 and the radiation source position S2 to each other, a straight line L3 connecting the corresponding point P33 of the projection image G3 and the radiation source position S3 to each other, a straight line L4 connecting the corresponding point P34 of the projection image G4 and the radiation source position S4 to each other, and a straight line L5 connecting the corresponding point P35 of the projection image G5 and the radiation source position S5 to each other. Then, as shown in FIG. 17, the coordinate positions of the intersections of the plurality of straight lines L1 to L5 as viewed from the direction perpendicular to the movement of the X-ray source 16 are calculated. It is assumed that the calculated intersections are first intersections. The coordinate position of each first intersection is a position of the x coordinate and the z coordinate. Here, the radiation source positions S1 to S5, the position of the detection surface of the radiation detector 15 where the projection images G1 to G5 are generated, and the positions of the corresponding points P31 to P35 are known. Therefore, the structure position specifying unit 33 calculates the straight lines L1 to L5 and the coordinate position of the first intersection based on the radiation source positions S1 to S5, the position of the detection surface of the radiation detector 15 where the projection images G1 to G5 are generated, and the positions of the corresponding points P31 to P35. Then, the structure position specifying unit 33 calculates a reference point B0 from the plurality of first intersections.

Here, in the case of performing tomosynthesis imaging, the straight lines connecting the radiation source positions and the corresponding points calculated as described above are not parallel to each other. Therefore, in a case where the number of radiation source positions is N, the number of first intersections is $N \times (N-1)/2$. Assuming that the x coordinate and the z coordinate at the first intersection are xk and zk (where k is the number of intersections), the structure position specifying unit 33 calculates the x coordinate xc and the z coordinate zc of the reference point B0 according to the following Equation (1). The reference point B0 indicates the x coordinate and the z coordinate of the structure position.

$$xc = \Sigma xk/(N \times (N-1)/2)$$

$$zc = \Sigma zk/(N \times (N-1)/2) \qquad (1)$$

Figure 18:
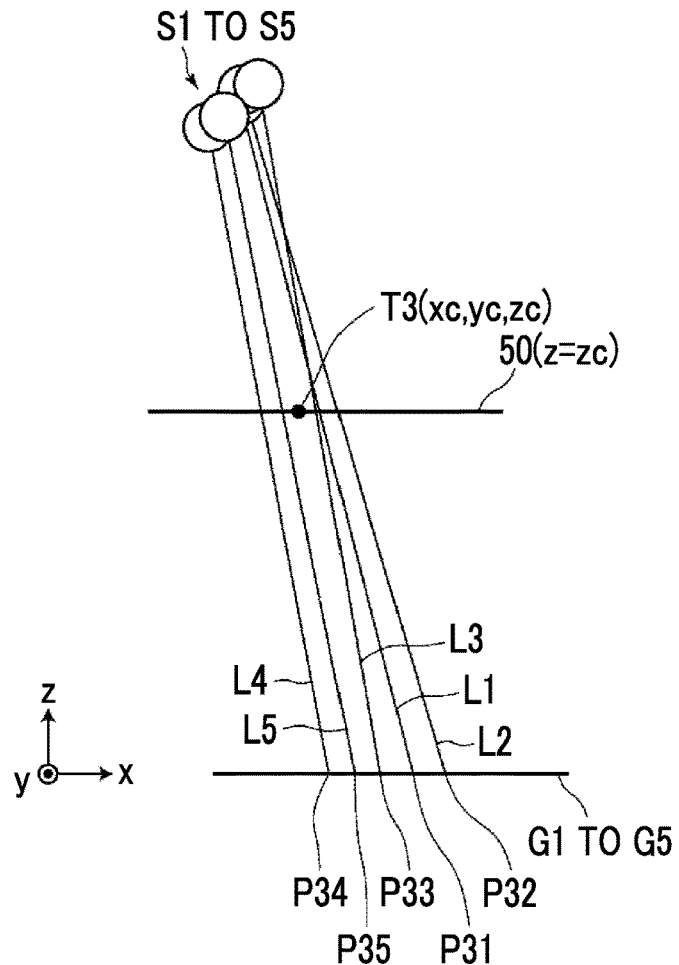
FIG. 18 is a diagram illustrating the specification of a structure position in the fourth embodiment.

On the other hand, the X-ray source 16 does not move completely in accordance with a predetermined path but moves in a three-dimensional manner with some blurring. For this reason, in the fourth embodiment, as shown in FIG. 18, the structure position specifying unit 33 sets a plane 50 that includes the reference point B0 calculated by Equation (1) and is parallel to the detection surface of the radiation detector 15. The z coordinate of the plane 50 is zc. Then, the structure position specifying unit 33 calculates, as coordinate positions of second intersections, coordinate positions of intersections between the plane 50 and a plurality of straight lines as viewed from the direction parallel to the movement direction of the X-ray source 16. Assuming that the y coordinate of each of the intersections between the plane 50 and the straight lines L1 to L5 is yk, the structure position specifying unit 33 calculates the y coordinate yc of the structure position according to the following Equation (2).

$$yc = \Sigma yk/N \quad (2)$$

In the fourth embodiment, the structure position specifying unit 33 specifies a structure position T3 as described above. Accordingly, the coordinate position of the structure position T3 is (xc, yc, zc). In a case where the structure position T3 is specified as described above, the structure position specifying unit 33 specifies a projection position of the structure position T3 in the projection image Gi as in the second embodiment described above. At the time of switching display of the projection image Gi, the display controller 34 displays the projection positions of the structure position T3 in the projection images G1 to G3 so as to match the center position (that is, the intersection of diagonals of the screen) of the display unit 3.

In the fourth embodiment, a plurality of structure position candidates in the breast M may be detected, and one structure position may be specified from the plurality of structure position candidates. In this case, the structure position specifying unit 33 specifies a plurality of corresponding points indicating the same structure among a plurality of projection images Gi, and specifies a structure position as a structure position candidate in the same manner as described above for each of the plurality of corresponding points. Then, for each of the plurality of structure position candidates, the structure position specifying unit 33 calculates variations of the first and second intersections, from which the structure position candidates have been calculated, from the structure position candidate. As the variations, statistical values of the distances from the structure position candidate to the first and second intersections are used. As the statistical values, an average value, a median value, or a maximum value of distances can be used. In a case where body movement occurs during tomosynthesis imaging, the statistical value of the distance becomes a large value. For this reason, the structure position specifying unit 33 specifies a structure position candidate with the largest calculated variation as a structure position. As a result, at the time of performing switching display of the projection image Gi on the display unit 3, it is possible to more easily check whether or not body movement has occurred.

In the third embodiment described above, at the time of specifying a structure position in a tomographic image using corresponding points in the projection image Gi, the structure position may be specified in the same manner as in the fourth embodiment. Also in the case of specifying a plurality of structure positions in a tomographic image in the third embodiment, at the time of specifying a structure position in a tomographic image using corresponding points in the projection image Gi, structure position candidates may be calculated in the same manner as in the case of specifying a plurality of corresponding points in the fourth embodiment, and one structure position may be specified.

Figure 19:
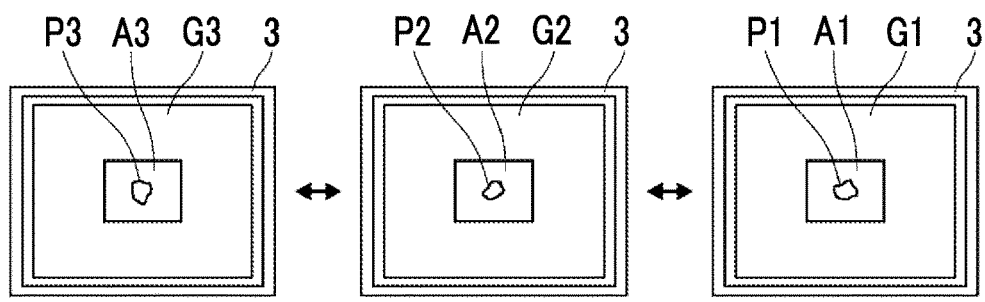
FIG. 19 is a diagram showing an example of switching display of projection images.

In each of the embodiments described above, a plurality of projection images Gi are switching-displayed on the display unit 3. However, only a region with a specific size including the projection positions of the structure position T1 in a plurality of projection images Gi may be switching-displayed on the display unit 3. For example, as shown in FIG. 19, only regions A1 to A3 with specific sizes including the projection positions P1 to P3 of the structure position T1 may be switching-displayed on the display unit 3.

Figure 20:
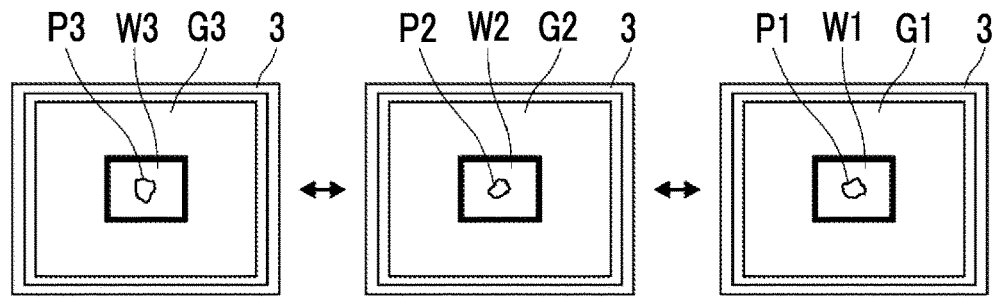
FIG. 20 is a diagram showing an example of switching display of projection images.
Figure 21:
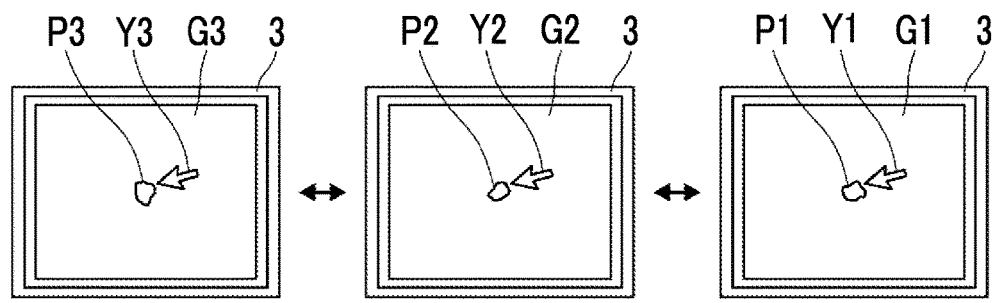
FIG. 21 is a diagram showing an example of switching display of projection images.
Figure 22:
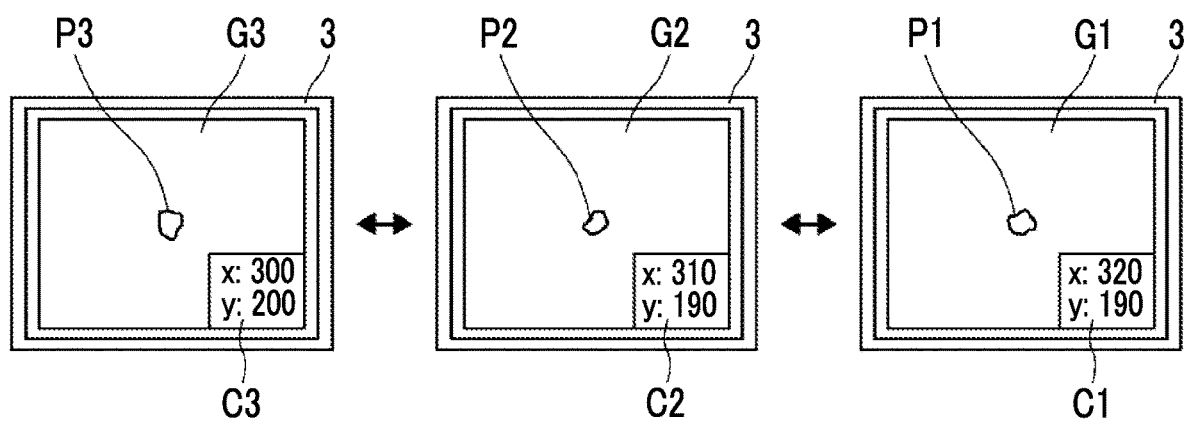
FIG. 22 is a diagram showing an example of switching display of projection images.
Figure 23:
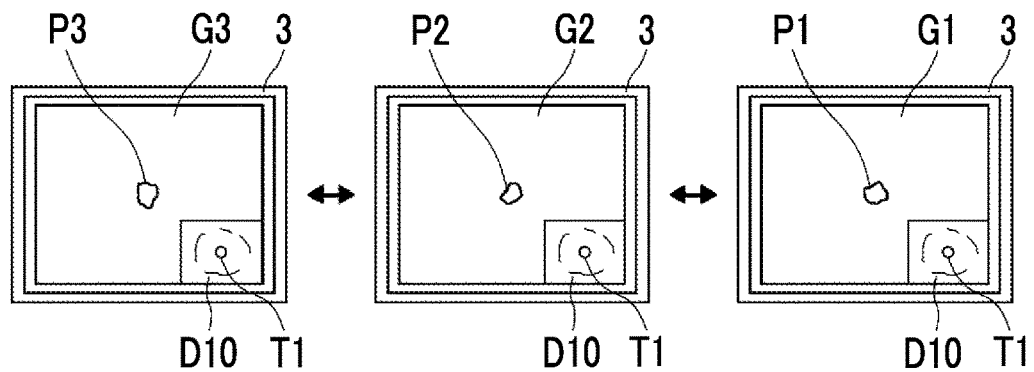
FIG. 23 is a diagram showing an example of switching display of projection images.
Figure 24:
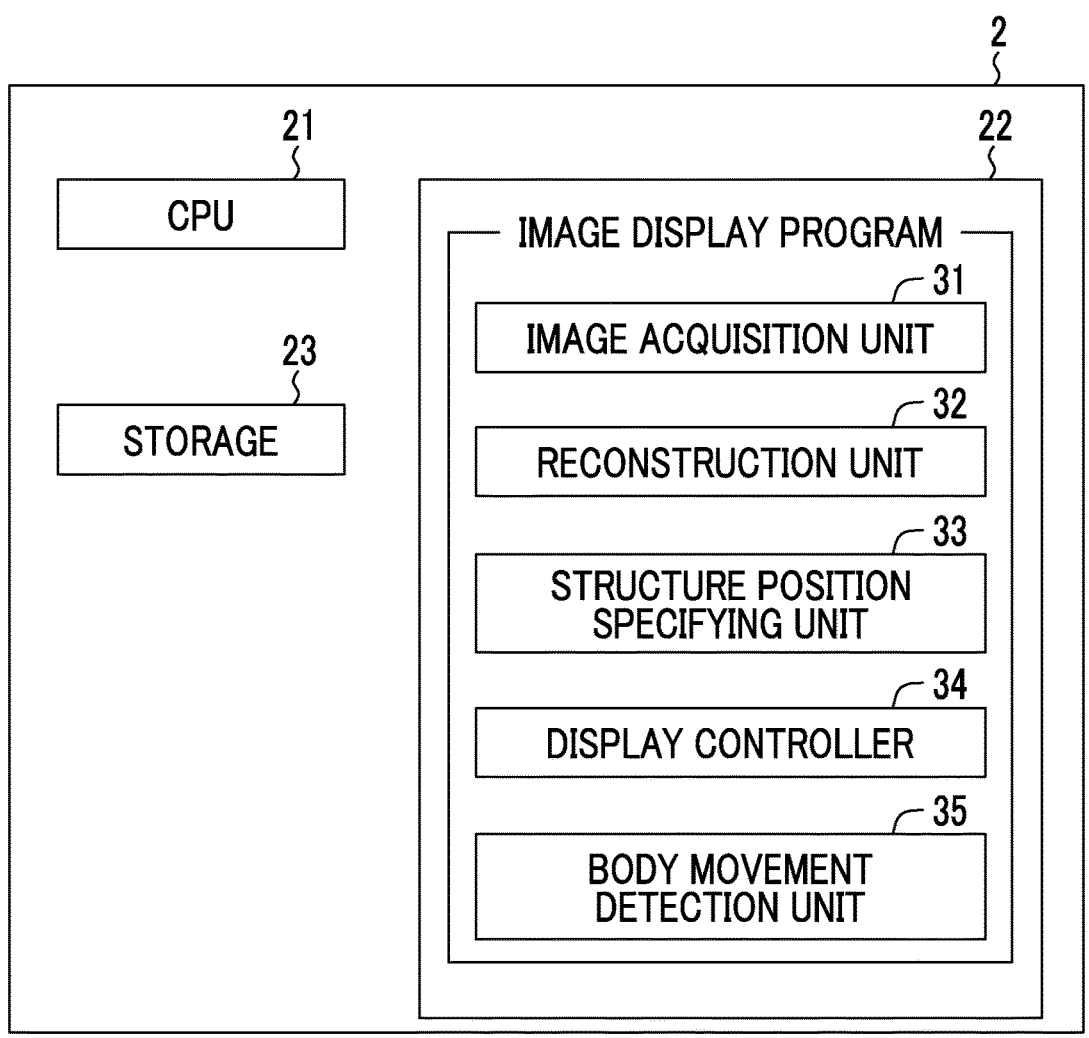
FIG. 24 is a diagram showing the schematic configuration of another example of the image display device.
Figure 25:
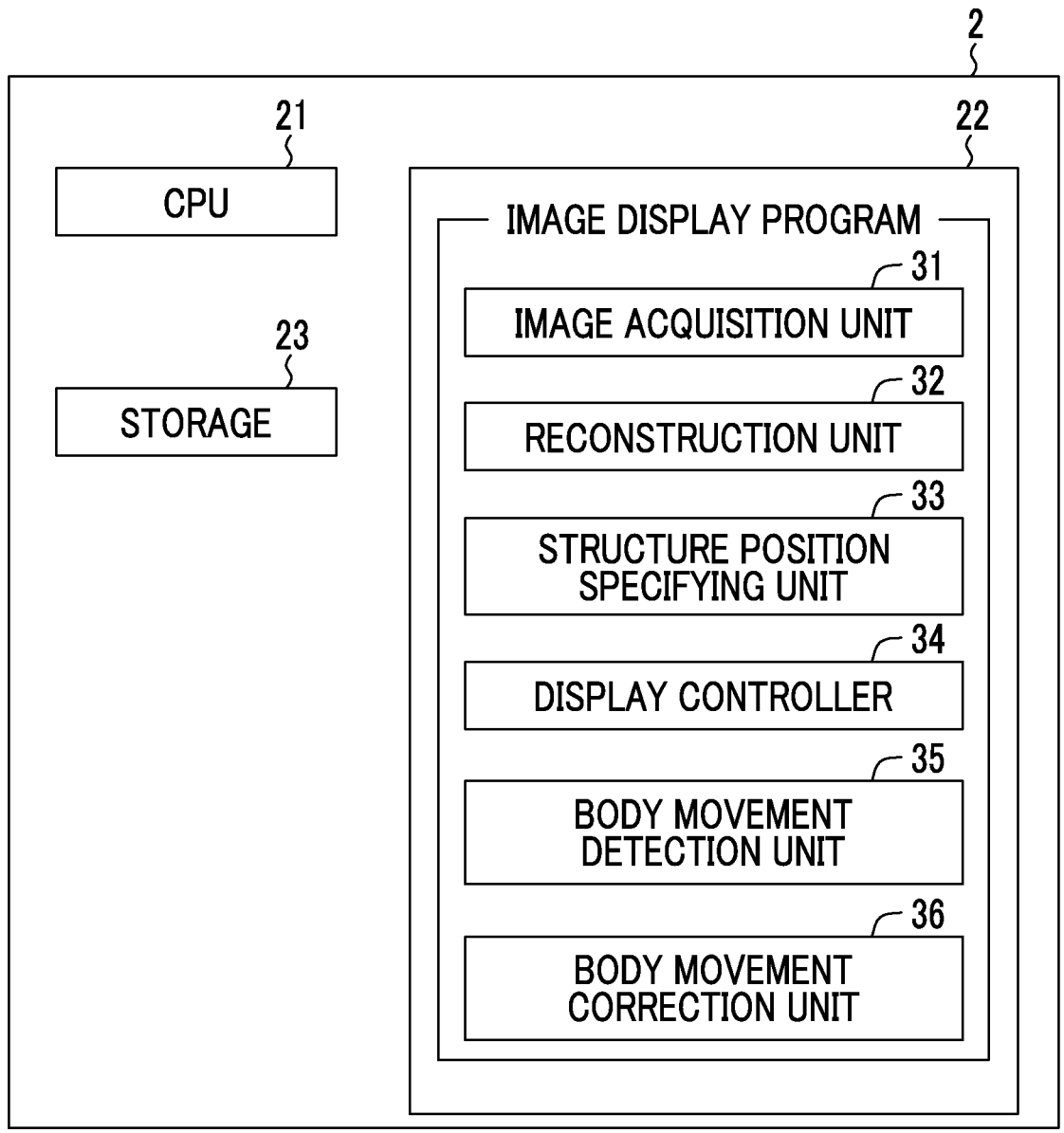
FIG. 25 is a diagram showing the schematic configuration of another example of the image display device.
Figure 26:
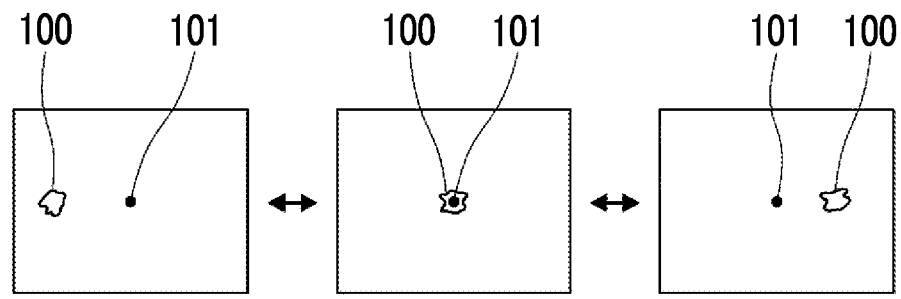
FIG. 26 is a diagram illustrating the display of a projection image in the related art.

In addition, although a plurality of projection images Gi are switching-displayed on the display unit 3 in each of the embodiments described above, the projection positions of the structure position T1 in a plurality of projection images Gi may be emphasized and displayed. Specifically, frames W1 to W3 surrounding the projection positions of the structure position T1 in a plurality of projection images Gi may be displayed as shown in FIG. 20, or arrows Y1 to Y3 indicating the projection positions of the structure position T1 in a plurality of projection images Gi may be given as shown in FIG. 21. Alternatively, as shown in FIG. 22, coordinates C1 to C3 of the projection values of the structure position T1 in a plurality of projection images Gi may be displayed. In addition, as shown in FIG. 23, a tomographic image D10 in which the structure position T1 is specified may be displayed. In each of the embodiments described above, during tomosynthesis imaging, it may be detected whether or not body movement of the breast M has occurred, and the processing according to each of the embodiments described above may be performed so that projection images are switching-displayed only in a case where body movement occurs. In this case, the occurrence of body movement may be notified by displaying the fact on the display unit 3 or by outputting a sound. In order to detect body movement, a sensor for detecting body movement may be provided in the radiation image capturing apparatus 1. Alternatively, as shown in FIG. 24, a body movement detection unit 35 may be provided in the image display device according to the present embodiment, so that the body movement detection unit 35 detects body movement using the projection image Gi. As a method for detecting body movement, for example, as disclosed in JP2012-055474A, it is possible to use any known method, such as a method of calculating a local movement amount of an image expressed by body movement of a local region between projection images Gi, that is, a local movement vector, and detecting the movement based on the local movement vector. In a case where body movement occurs, body movement correction may be performed on the projection image Gi, and the processing according to each of the embodiments described above may be performed using the projection image Gi after the body movement correction is performed. In this case, as shown in FIG. 25, in addition to the body movement detection unit 35, a body movement correction unit 36 may be provided in the image display device according to the present embodiment, so that the body movement correction unit 36 performs body movement correction. As a method of body movement correction, for example, as disclosed in JP2017-063907A, it is possible to use any known method, such as a method of calculating a local movement vector, which represents a movement amount and a movement direction between projection images with respect to a reference projection image, for each local region between projection images Gi and performing processing for translating, rotating, and scaling the projection image Gi for each local region. In this manner, by performing body movement correction and performing the processing according to each of the embodiments described above using the projection image Gi after the body movement correction is performed, it is possible to easily check whether or not the body movement correction has been performed appropriately.

In each of the embodiments described above, the X-ray source 16 is moved to perform tomosynthesis imaging. However, the radiation detector 15 may be moved to perform tomosynthesis imaging. Alternatively, both of the X-ray source 16 and the radiation detector 15 may be moved to perform tomosynthesis imaging.

In each of the embodiments described above, the subject is the breast M. However, the present disclosure is not limited thereto, and it is a matter of course that any part, such as the chest or abdomen of a human body, may be the subject.

What is claimed is:

1. An image display device, comprising:
  a processor that is configured to:
   acquire a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source;
   specify one structure position in the subject; and
   specify projection positions of the structure position in the plurality of projection images and perform switching display of the plurality of projection images on a display unit such that the projection positions match a predetermined position on the display unit.

2. The image display device according to claim 1, wherein the processor is configured to:
  generate a tomographic image in at least one tomographic plane of the subject by reconstructing the plurality of projection images,
  specify unit specifies feature points included in the tomographic image, calculate a distribution of signal values of the feature points in a direction in which the tomographic planes are aligned, and specify, as the structure position, a position having a highest signal value or a position having a lowest signal value in the distribution.

3. The image display device according to claim 2,
  wherein the processor is configured to calculate the signal value distribution based on other tomographic images having a distance between tomographic planes smaller than that in a case of the tomographic image.

4. The image display device according to claim 1,
  wherein the processor is configured to detect a plurality of structure position candidates in the subject, and specify the one structure position from the plurality of structure position candidates.

5. The image display device according to claim 4, wherein the processor is configured to:
  generate a tomographic image in at least one tomographic plane of the subject by reconstructing the plurality of projection images,
  specify a plurality of feature points included in the tomographic image, calculate a distribution of signal values in a direction in which the tomographic plane is aligned for each of the plurality of feature points, specify a position having a highest signal value or a position having a lowest signal value in the distribution as the structure position candidate for each of the plurality of feature points, and specify a structure position candidate having a highest signal value or a structure position candidate having a lowest signal value, among the plurality of structure position candidates, as the structure position.

6. The image display device according to claim 5,
  wherein the processor is configured to calculate the signal value distribution based on other tomographic images having a distance between tomographic planes smaller than that in a case of the tomographic image.

7. The image display device according to claim 1,
  wherein the processor is configured to specify corresponding points indicating the same structure among the plurality of projection images, reconstruct corresponding points among the plurality of projection images, and specify a position including the corresponding points in the subject as the structure position.

8. The image display device according to claim 4,
  wherein the processor is configured to specify a plurality of corresponding points indicating the same structure among the plurality of projection images, reconstruct each of the plurality of corresponding points among the plurality of projection images, specify positions including the plurality of corresponding points in the subject as the plurality of structure position candidates, and specify a structure position candidate having a highest signal value or a structure position candidate having a lowest signal value, among the plurality of structure position candidates, as the structure position.

9. The image display device according to claim 1,
  wherein the processor is configured to specify at least one corresponding point indicating the same structure among the plurality of projection images, set a plurality of straight lines connecting corresponding points in the plurality of projection images and a radiation source position at the time of acquiring each of the plurality of projection images, calculate a plurality of first intersections of the plurality of straight lines as viewed from a direction perpendicular to a movement direction of the radiation source, sets a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, and specify the structure position based on the reference point and the second intersections.

10. The image display device according to claim 4,
  wherein the processor is configured to specify a plurality of corresponding points indicating the same structure among the plurality of projection images, set a plurality of straight lines connecting the plurality of corresponding points in the plurality of projection images and a radiation source position at the time of acquiring each of the plurality of projection images, calculate a plurality of first intersections of the plurality of straight lines as viewed from a direction perpendicular to a movement direction of the radiation source, set a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, specify the plurality of structure position candidates based on the reference point and the second intersections, and specify the structure position from the plurality of structure position candidates based on variations of the plurality of first intersections and the plurality of second intersections for each of the plurality of structure position candidates.

11. The image display device according to claim 1, wherein the processor is configured to:
generate a tomographic image in at least one tomographic plane of the subject by reconstructing the plurality of projection images,
specify feature points included in the tomographic image, project the feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, reconstruct corresponding points among the plurality of projection images, and specify a position including the corresponding points in the subject as the structure position.

12. The image display device according to claim 4, wherein the processor is configured to:
generate a tomographic image in at least one tomographic plane of the subject by reconstructing the plurality of projection images,
specify a plurality of feature points included in the tomographic image, project the plurality of feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, reconstruct corresponding points among the plurality of projection images, specify positions including the corresponding points in the subject as the plurality of structure position candidates, and specify a structure position candidate having a highest signal value or a structure position candidate having a lowest signal value, among the plurality of structure position candidates, as the structure position.

13. The image display device according to claim 4, wherein the processor is configured to:
generate a tomographic image in at least one tomographic plane of the subject by reconstructing the plurality of projection images,
specify a plurality of feature points included in the tomographic image, project the plurality of feature points onto the plurality of projection images, specify feature projection positions corresponding to the feature points in the plurality of projection images, set regions including the feature projection positions in the plurality of projection images, specify at least one corresponding point indicating the same structure among the regions in the plurality of projection images, sets a plurality of straight lines connecting the plurality of corresponding points in the plurality of projection images and a radiation source position at the time of acquiring each of the plurality of projection images, calculate a plurality of first intersections of the plurality of straight lines as viewed from a direction perpendicular to a movement direction of the radiation source, set a reference point based on the first intersections, calculate, in a plane that includes the reference point and is parallel to a detection surface of the detection unit, a plurality of second intersections of the plurality of straight lines and the plane parallel to the detection surface of the detection unit as viewed from a direction parallel to the movement direction of the radiation source, specify the plurality of structure position candidates based on the reference point and the second intersections, and specify the structure position from the plurality of structure position candidates based on variations of the plurality of first intersections and the plurality of second intersections for each of the plurality of structure position candidates.

14. The image display device according to claim 1, wherein the processor is configured to perform switching display of only a region with a specific size including the projection positions in the plurality of projection images on the display unit.

15. The image display device according to claim 1, wherein the processor is configured to cause display of a tomographic image of a tomographic plane including the structure position on the display unit.

16. The image display device according to claim 15, wherein the processor is configured to cause display of the structure position in the projection image on the display unit such that the structure position in the projection image is emphasized.

17. The image display device according to claim 1, wherein the subject is a breast.

18. The image display device according to claim 1, wherein the processor is configured to:
detect body movement of the subject,
specify the structure position in a case where the body movement is detected, and
perform switching display of the plurality of projection images on the display unit in a case where the body movement is detected.

19. The image display device according to claim 1, wherein the processor is configured to:
detect body movement of the subject; and
perform body movement correction on the projection image in a case where the body movement is detected,
specify the projection positions in the plurality of projection images on which body movement correction has been performed and perform switching display of the plurality of projection images, on which body movement correction has been performed, on the display unit such that the projection positions match a predetermined position on the display unit.

20. An image display method, comprising:
acquiring a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source;
specifying one structure position in the subject; and
specifying projection positions of the structure position in the plurality of projection images and performing switching display of the plurality of projection images on a display unit such that the projection positions match a predetermined position on the display unit.

21. A non-transitory computer-readable storage medium that stores an image display program causing a computer to execute:

a step of acquiring a plurality of projection images corresponding to a plurality of radiation source positions, the plurality of projection images being generated by tomosynthesis imaging in which a radiation source is moved relative to a detection unit such that radiation is emitted to a subject at the plurality of radiation source positions according to movement of the radiation source;

a step of specifying one structure position in the subject; and a step of specifying projection positions of the structure position in the plurality of projection images and performing switching display of the plurality of projection images on a display unit such that the projection positions match a predetermined position on the display unit.

* * * * *